US012458215B2

(12) United States Patent
Yanuma

(10) Patent No.: US 12,458,215 B2
(45) Date of Patent: Nov. 4, 2025

(54) TREATMENT TOOL FOR ENDOSCOPE AND METHOD FOR USING TREATMENT TOOL FOR ENDOSCOPE

(71) Applicant: Olympus Corporation, Tokyo (JP)

(72) Inventor: Yutaka Yanuma, Tokyo (JP)

(73) Assignee: Olympus Corporation, Tokyo (JP)

( * ) Notice: Subject to any disclaimer, the term of this patent is extended or adjusted under 35 U.S.C. 154(b) by 358 days.

(21) Appl. No.: 18/179,078

(22) Filed: Mar. 6, 2023

(65) Prior Publication Data

US 2023/0200633 A1 Jun. 29, 2023

Related U.S. Application Data

(63) Continuation of application No. PCT/JP2020/037807, filed on Oct. 6, 2020.

(51) Int. Cl.
*A61B 1/00* (2006.01)
*A61B 1/018* (2006.01)

(52) U.S. Cl.
CPC .......... *A61B 1/018* (2013.01); *A61B 1/00042* (2022.02)

(58) Field of Classification Search
CPC . A61B 1/018; A61B 1/00042; A61B 1/00137; A61B 1/0125; A61B 1/00128; A61B 1/00133; A61B 1/00121; A61B 1/00087
See application file for complete search history.

(56) References Cited

U.S. PATENT DOCUMENTS 6,346,093 B1 * 2/2002 Allman ............. A61M 25/0097 604/164.03
2009/0062769 A1 * 3/2009 Graves ............ A61M 25/09041 604/510

(Continued)

FOREIGN PATENT DOCUMENTS

| | | |
|---|---|---|
| CN | 105979895 | 9/2016 |
| JP | 2002543937 A | 12/2002 |
| JP | 2002543938 A | 12/2002 |

(Continued)

OTHER PUBLICATIONS

"International Application Serial No. PCT JP2020 037807, International Search Report dated Dec. 8, 2020", w English Translation, (Dec. 8, 2020), 5 pgs.

(Continued)

*Primary Examiner* — Timothy J Neal
(74) *Attorney, Agent, or Firm* — Schwegman Lundberg & Woessner, P.A.

(57) ABSTRACT

The treatment tool for an endoscope includes a sheath having a lumen into which a guide wire is insertable, a distal end portion in which a distal end opening communicating with the lumen is formed, a proximal end portion in which a proximal end opening communicating with the lumen is formed, and a sheath slit in which a proximal end communicates with the proximal end opening and which is elongated along a longitudinal axis direction toward the distal end portion; and a funnel tube into which the sheath is insertable, the funnel tube including a through-hole formed on a side surface of the funnel tube at a position corresponding to the proximal end opening of the sheath, and a funnel slit elongated in the longitudinal axis direction.

2 Claims, 17 Drawing Sheets

(56) References Cited

U.S. PATENT DOCUMENTS

| | | | |
|---|---|---|---|
| 2018/0042462 | A1 | 2/2018 | Yanuma |
| 2019/0008364 | A1 | 1/2019 | Yamanaka |

FOREIGN PATENT DOCUMENTS

| | | | |
|---|---|---|---|
| JP | 4651823 | B2 | 3/2011 |
| JP | 2016202231 | A | 12/2016 |
| JP | 2021529580 | | 11/2021 |
| WO | WO-0069499 | A1 | 11/2000 |
| WO | WO-0069500 | A1 | 11/2000 |
| WO | WO-2017168762 | A1 | 10/2017 |

OTHER PUBLICATIONS

"Japanese Application Serial No. 2022-554994, Notice of Allowance dated Mar. 12, 2024", w English Translation, (Mar. 12, 2024), 6 pgs.

"International Application Serial No. PCT/JP2020/038591, International Search Report dated Dec. 8, 2020", w/ English Translation, (Dec. 8, 2020), 5 pgs.

"Chinese Application No. 202110340697.7, Office Action dated Dec. 19, 2024", w English Translation, (Dec. 19, 2024), 26.

* cited by examiner

TREATMENT TOOL FOR ENDOSCOPE AND METHOD FOR USING TREATMENT TOOL FOR ENDOSCOPE

The invention relates to a treatment tool for an endoscope and a method for using the treatment tool for an endoscope. This application is a continuation application based on International Patent Application No. PCT/JP2020/037807 filed on Oct. 6, 2020, the contents of which are incorporated herein by reference.

BACKGROUND

When treating disease relating to a hollow organ of a human body, there is a case of inserting a guide wire into the luminal organ by using an endoscope in order to introduce a treatment tool into a treatment target portion of a luminal organ. In the case of such an operation of the endoscope, the endoscope is inserted into the body, and the guide wire is indwelled to the hollow organ to be treated from an outside of the body by using a cannula inserted into an insertion path of the endoscope. After that, the treatment tool is inserted into the hollow organ along with the indwelled guide wire. During treatment, there is a case in which a plurality of the treatment tools, for example, balloons for expanding a lumen or supplying contrast medium, and an incision tool or the like, are sequentially changed. In the related art, catheters for each treatment tool are removed and inserted each time a treatment tool is changed.

On the other hand, for example, the specification of Japanese Patent No. 4,651,823 discloses a catheter in which a C-channel slit is formed on a proximal portion of the shaft, and in which a guide wire port provided in the vicinity of the operation part communicates with the C-channel slit. In the catheter disclosed in the specification of Japanese Patent No. 4,651,823, the guide wire is inserted into the C-channel and exposed from the guide wire port. The catheter disclosed in the specification of Japanese Patent No. 4,651,823 is configured such that the guide wire can be drawn out from the guide wire port and the guide wire can be easily inserted and removed with respect to the endoscope insertion portion. As a result, the guide wire can be removed from the insertion tool for the guide wire while remaining inside the guide wire lumen of the catheter.

SUMMARY

A treatment tool for an endoscope according to the disclosure includes: a sheath including a lumen into which a guide wire is insertable, a distal end portion in which a distal end opening communicating with the lumen is formed, a proximal end portion in which a proximal end opening communicating with the lumen is formed, and a sheath slit in which a proximal end communicates with the proximal end opening and which is elongated along a longitudinal axis direction toward the distal end portion; and a funnel tube into which the sheath is insertable, the funnel tube including a through-hole formed on a side surface of the funnel tube at a position corresponding to the proximal end opening of the sheath, and a funnel slit elongated in the longitudinal axis direction. The funnel tube is capable of changing between a first state and a second state by rotating about the longitudinal axis with respect to the sheath, in the first state, the guide wire is restricted to enter the sheath slit, and in the second state, the guide wire is capable of being inserted into the sheath slit.

DETAILED DESCRIPTION OF EXEMPLARY EMBODIMENTS

First Embodiment

Figure 1:
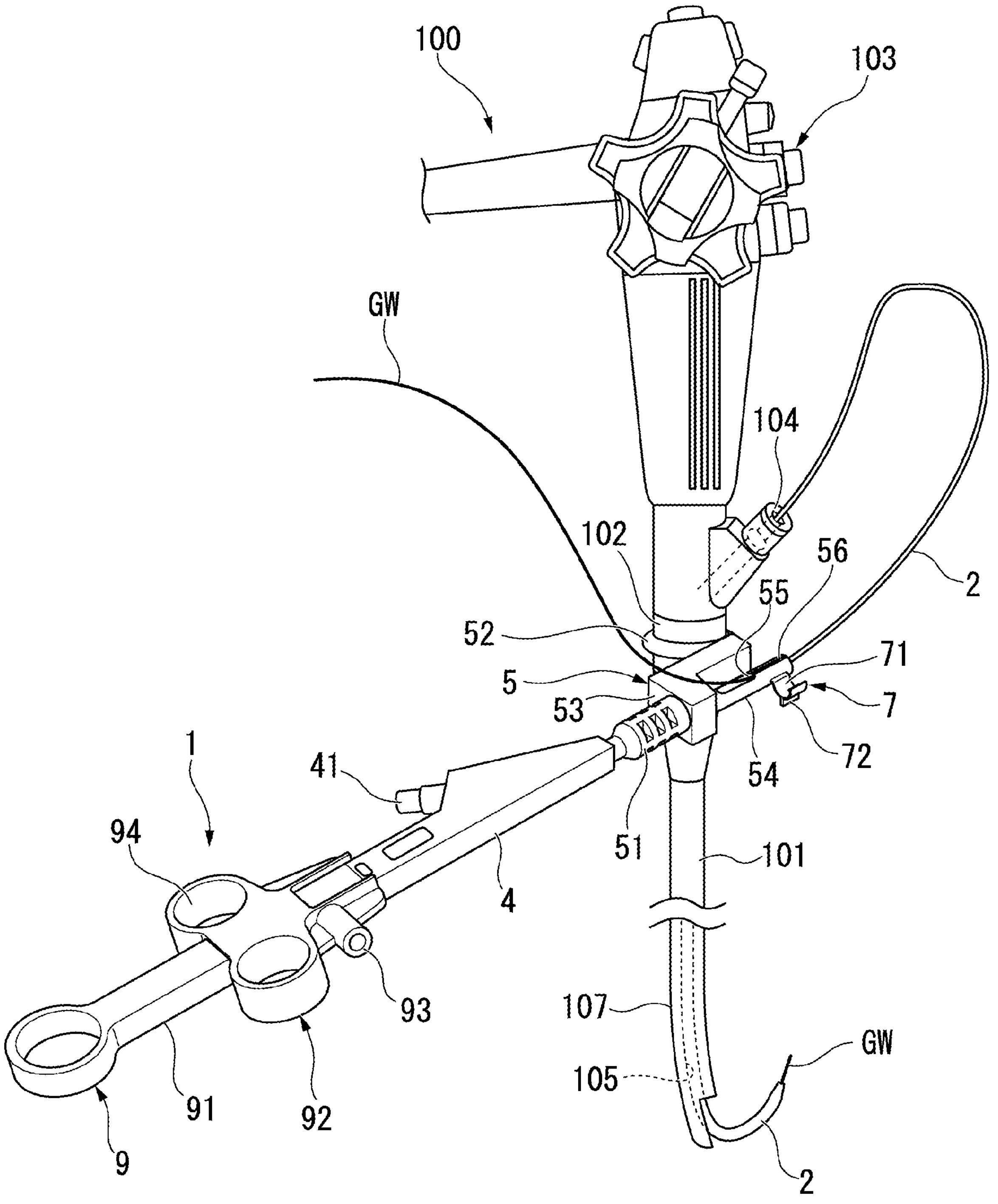
FIG. 1 is a perspective view showing a usage aspect of a treatment tool for an endoscope according to a first embodiment.

A treatment tool for an endoscope according to a first embodiment of the present disclosure will be described with reference to FIGS. 1 to 10. FIG. 1 is an overall view showing a usage embodiment of a treatment tool 1 for an endoscope according to the embodiment by inserting it into a treatment tool channel 105 of an endoscope device 100.

As shown in FIG. 1, the treatment tool 1 for an endoscope according to the present embodiment is a medical instrument used together with the endoscope device 100 for incising living tissue inside a body. The endoscope device 100 according the embodiment has an active bending portion 107 provided at an endoscope insertion portion 101 configured to be inserted into the body. The active bending portion 107 is configured to be capable of performing a bending action by manipulating a manipulator 103.

In the embodiment, an example is described in which the treatment tool 1 for an endoscope (hereinafter, referred to as a “treatment tool 1”) is inserted into a side view type endoscope 100 suitable for observing a duodenal papilla. The side view type endoscope 100 includes, for example, the endoscope insertion portion 101, a grip portion 102, the manipulator 103, a forceps plug 104, the treatment tool channel 105, an elevator and an imaging portion which are not shown. The endoscope insertion portion 101 is a portion to be inserted into the body. The manipulator 103 is a portion to be operated by the operator. In the following description, a side where the manipulator 103 is provided in the endoscope device 100 will be referred as a proximal side P, and an end part side of the endoscope insertion portion 101 and a side of protruding the treatment tool 1 will be referred as a distal side D. Similarly, a side of an operation portion 9 (which will be described later) of the treatment tool 1 will be referred as the proximal side P, and a side of an end portion, which is inserted into the body, of a sheath 2 on the opposite side to the operation portion 9 in a longitudinal direction will be referred as the distal side D.

The grip portion 102 is arranged at the proximal end of the endoscope insertion portion 101. The forceps plug 104 is arranged on a part of the grip portion 102. The treatment tool channel 105 communicates with the forceps plug 104 and is formed in the endoscope insertion portion 101. The elevator is provided to change a direction of the treatment tool 1 or the like protruded from the treatment tool channel 105 at a distal end of the treatment tool channel 105 with respect to a central axis of the endoscope insertion portion 101. The imaging portion is provided at the distal end of the endoscope insertion portion 101.

The treatment tool 1 is inserted into the treatment tool channel 105 via the forceps plug 104 and is arranged to be capable of protruding from and retracting to the distal end of the endoscope insertion portion 101. The treatment tool 1 includes the sheath 2, the operating portion 9, a base portion 4, and a coupling portion 5. The operating portion 9 is provided at the proximal end of the treatment tool 1. The sheath 2 is provided at the distal side D of the treatment tool 1. The sheath 2 and the operating portion 9 are connected via the base portion 4 and the coupling portion 5.

Figure 4:
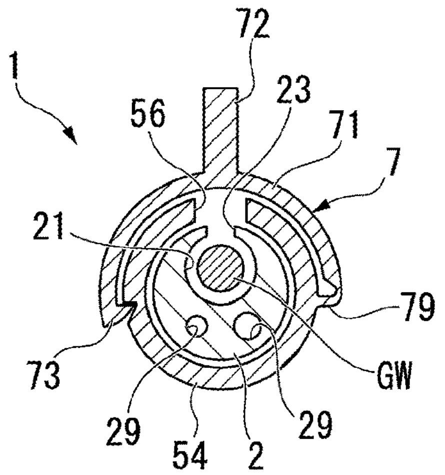
FIG. 4 is a cross-sectional view taken along line IV-IV of FIG. 2.
Figure 5:
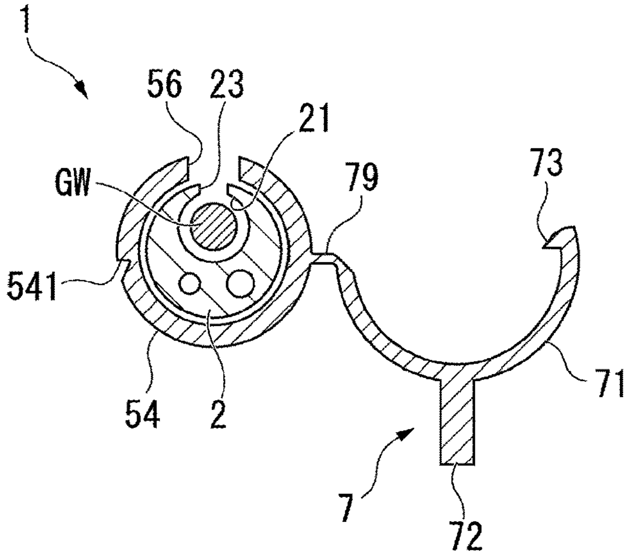
FIG. 5 is a cross-sectional view taken along line V-V of FIG. 3.
Figure 6:
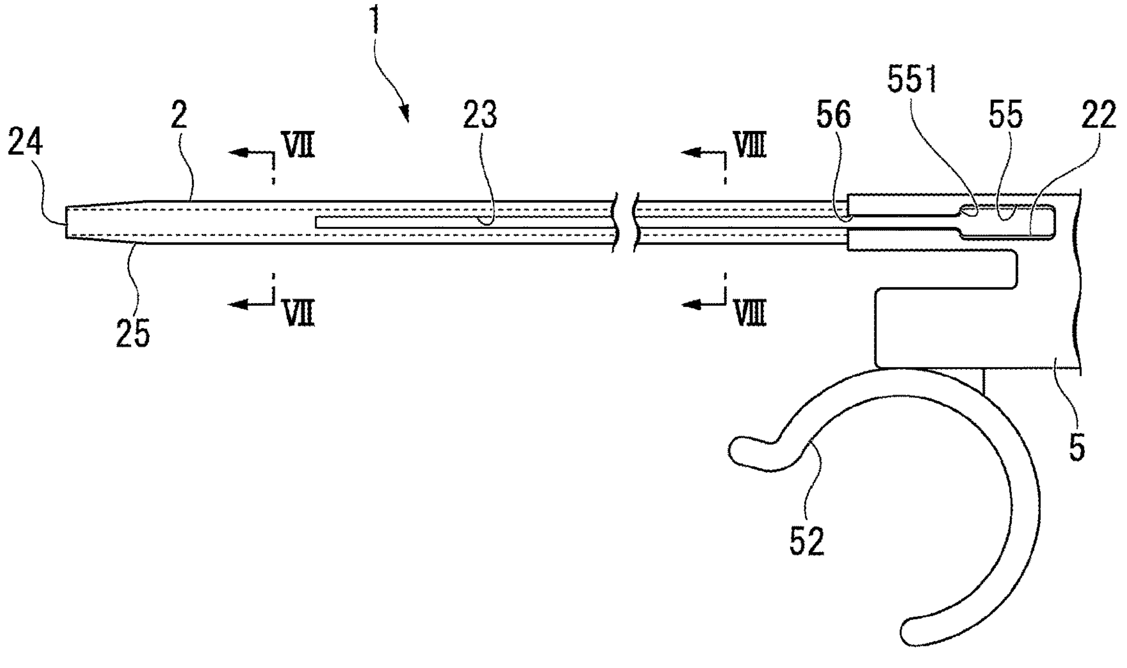
FIG. 6 is a side view showing the distal end portion of the treatment tool for an endoscope according to the first embodiment.
Figure 7:
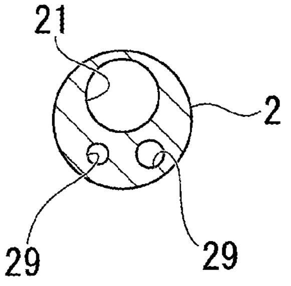
FIG. 7 is a cross-sectional view taken along line VII-VII of FIG. 6.
Figure 8:
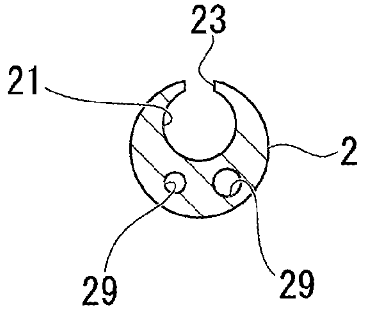
FIG. 8 is a cross-sectional view taken along line VIII-VIII of FIG. 6.

The sheath 2 is an elongated member inserted into the treatment tool channel 105. The sheath 2 is an elongated member having flexibility. In the embodiment, the sheath 2 is made of resin. As shown in FIGS. 4 and 5, a guide wire lumen 21 is formed in the sheath 2. As shown in FIGS. 6 to 8, the guide wire lumen 21 is formed over the whole length of the sheath 2 from a proximal end opening 22 at the proximal end of the sheath 2 to a distal end opening 24 at the distal end of the sheath 2. The guide wire lumen 21 is a lumen having a size that allows a guide wire GW to be capable of advancing and retracting. As shown in FIGS. 7 and 8, the guide wire lumen 21 is notched on an outward side of the sheath 2 in the radial direction, and has a C-channel structure having a substantially C-shape in a cross-sectional shape orthogonal to the longitudinal axis. A sheath slit 23 is formed at a C-channel portion. The sheath slit 23 is formed from a vicinity of the distal end opening 24 of the sheath 2 to the proximal end opening 22 of the sheath 2. The sheath slit 23 is elastically deformable. A width of the sheath slit 23 is slightly smaller than an outer diameter of the guide wire GW used in combination with the treatment tool 1. The sheath 2 is configured such that the guide wire GW inserted into the guide wire lumen 21 is capable of being drawn out toward an outside of the sheath 2 through the elastically deformable sheath slit 23. A region including a portion where the distal end opening 24 is arranged is referred as a distal end portion of the sheath 2. A region including a portion where the proximal end opening 22 is arranged is referred as a proximal end portion of the sheath 2.

As shown in FIGS. 7 and 8, one or more lumens 29 are formed in the sheath 2 other than the guide wire lumen 21. The lumen 29 functions as an injection path for a contrast medium, an injection path for fluid to a balloon, or an insertion path for a strand of a knife wire.

The operating portion 9 is a part to perform input for the operator to operate other treatment tools inserted into the sheath 2. The operating portion 9 includes a shaft 91 and a slider 92. The shaft 91 is fixed to the base portion 4, and elongates linearly along the longitudinal axis. The slider 92 is provided so as to be slidable along the longitudinal axis of the shaft 91.

The slider 92, may include, for example, a connector 93 which is connectable with a high-frequency power supply, and a finger hooking portion 94. The connector 93 is, for example, electrically connected with a proximal end of the knife wire described later. The finger hooking portion 94 is configured such that the operator’s finger can be inserted therein.

The base portion 4 is provided with an insertion port 41. The insertion port 41 communicates with a lumen of the sheath 2 described later. The insertion port 41 is, for example, configured such that contrast medium or fluid for a balloon is injected into the lumen 29 or the knife wire is inserted.

Figure 2:
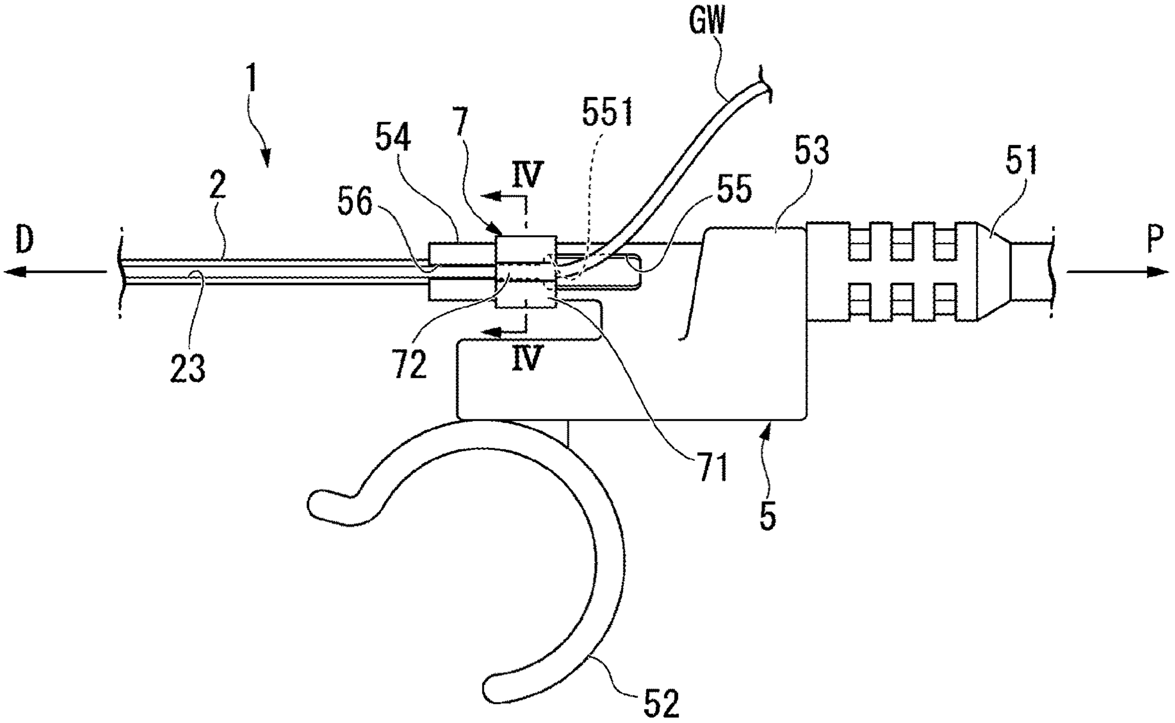
FIG. 2 is a side view showing a part of the treatment tool for an endoscope according to the first embodiment.
Figure 3:
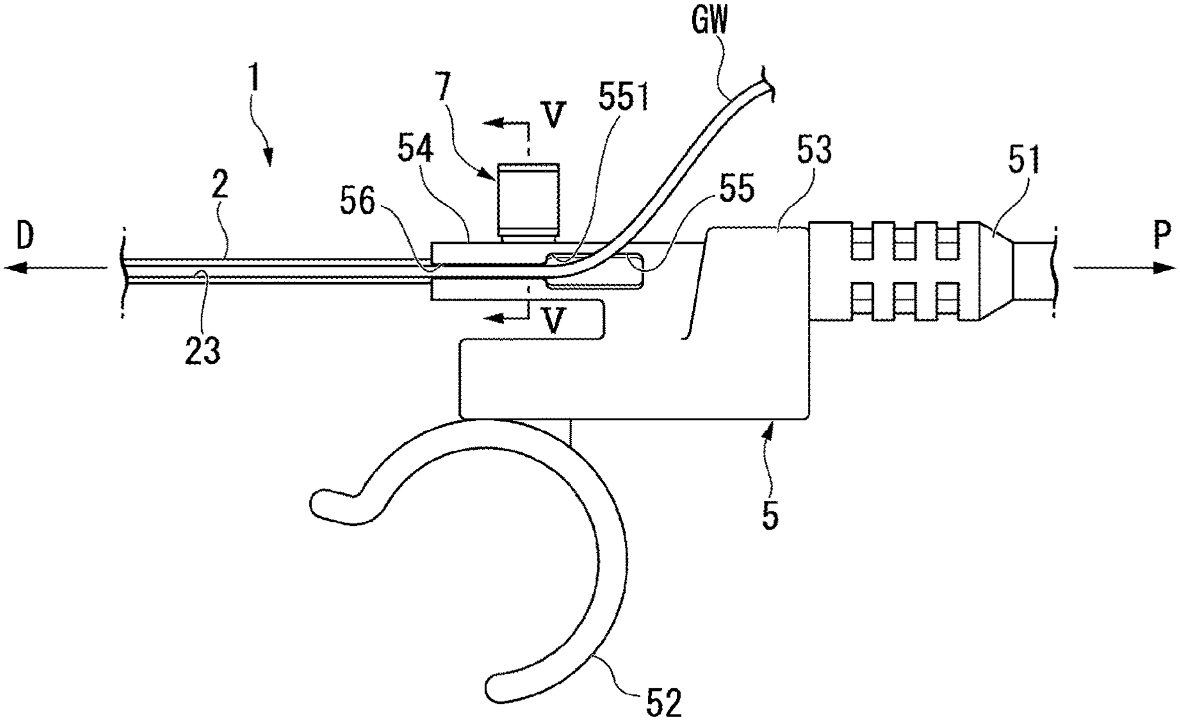
FIG. 3 is a side view showing the treatment tool for an endoscope according to the first embodiment.

The coupling portion 5 incudes a coupling main body 53, a proximal coupling portion 51, a hook 52, and a sheath coupling portion 54. The proximal coupling portion 51 is provided on a proximal end of the coupling main body 53. The proximal coupling portion 51 connects the base portion 4 with the coupling main body 53. The sheath coupling portion 54 and the hook 52 are provided on the distal portion of the coupling main body 53. The sheath coupling portion 54 is provided along the longitudinal axis at the distal side D of the operation portion 9 and the proximal coupling portion 51. As shown in FIGS. 2 and 3, the hook 52 is provided to protrude laterally from the sheath coupling portion 54. The hook 52 is a locking portion being lockable with the grip portion 102. As shown in FIG. 1, when the hook 52 is locked with the grip portion 102, a portion on the proximal side P from the coupling portion 5 of the treatment tool 1 is kept in a direction crossing the longitudinal axis of the endoscope device 100.

As shown in FIGS. 1 to 3, a proximal portion of the sheath 2 is inserted into the sheath coupling portion 54. A guide wire insertion port 55 is opened in the sheath coupling portion 54. A slit 56 is formed on the sheath 2 from a distal end 551 of the guide wire insertion port 55 to a distal end of the sheath coupling portion 54. The slit 56 is an example of a suppression slit. A width of the slit 56 is slightly larger than the outer diameter of the guide wire GW which is used in combination with the coupling portion 5. The guide wire insertion port 55 communicates with the guide wire lumen 21. As shown in FIGS. 3 to 5, the slit 56 is arranged close to the sheath slit 23 and the positions of each of the slits 56 and 23 in the circumferential direction are substantially the same.

The sheath coupling portion 54 is provided with a suppressor 7. The suppressor 7 is provided to suppress the guide wire GW protruded from the guide wire insertion port 55 from entering the slit 56. The suppressor 7 covers at least one of the slit 56 and the distal end 551 of the guide wire insertion port 55. The slit 56 is arranged at a position corresponding to the sheath slit 23, and the guide wire insertion port 55 is arranged at a position corresponding to the proximal end opening 22 of the sheath 2. Therefore, the suppressor 7 covers at least one of the sheath slit 23 and the proximal end opening 22. In the embodiment, the suppressor 7 is provided at a position to cover the slit 56.

FIG. 4 shows a cross-sectional view taken along line IV-IV of FIG. 2, and shows the suppressor 7 in the first state. FIG. 5 shows a cross-sectional view taken along line V-V of FIG. 3, and shows the suppressor 7 in the second state. As shown in FIGS. 4 and 5, the suppressor 7 includes a cover main body 71, a locking claw 73, a gripping protrusion 72, and a fixing portion 79 fixed to the sheath coupling portion 54. The cover main body 71 is an arcuate portion along an outer peripheral surface of the sheath coupling portion 54. The fixing portion 79 and the locking claw 73 are provided at an end portion in the circumferential direction of the arcuate portion of the cover main body 74. The gripping protrusion 72 is provided to protrude from the outer surface of the sheath coupling portion 54. The gripping protrusion 72 has a size and a shape such that the operator can grip the gripping protrusion 72 with their finger, and the gripping protrusion 72 may be provided at a position so as to be gripped by the operator. The locking claw 73 protrudes toward an inward side of the arcuate portion of the cover main body 71. The locking claw 73 is configured to be capable of locking with a concave 541 provided on the outer peripheral surface of the sheath coupling portion 54.

The suppressor 7 is provided so as to be openable and closable with the fixing portion 79 as a base point with respect to the sheath coupling portion 54. As shown in FIG. 4, a state in which the suppressor 7 covers the slit 56 and the locking claw 73 is locked with the concave 541 of the sheath coupling portion 54 is referred toes a first state. In the first state, the suppressor 7 covers at least one of the sheath slit 23 and the distal end 551 of the guide wire insertion port 55. As shown in FIG. 5, a state in which the cover main body 71 rotates around the fixing portion 79 in a direction away from the sheath coupling portion 54 and the slit 56 is opened is referred to as a second state. The suppressor 7 is configured to be capable of changing the first state and the second state by rotation action.

The suppressor 7 may be provided at a position to cover at least one of the slit 56 and the distal end 551 of the guide wire insertion port 55. For example, other than the example shown in FIGS. 4 and 5, a suppress portion may be provided at a position to cover a proximal end portion of the slit 56 and the distal end 551 of the guide wire insertion port 55. The suppressor 7 may be provided at a position preventing the guide wire GW from entering the slit 56 and the sheath slit 23, and does not prevent the guide wire GW from advancing and retracting in the guide wire insertion port 55.

Figure 36:
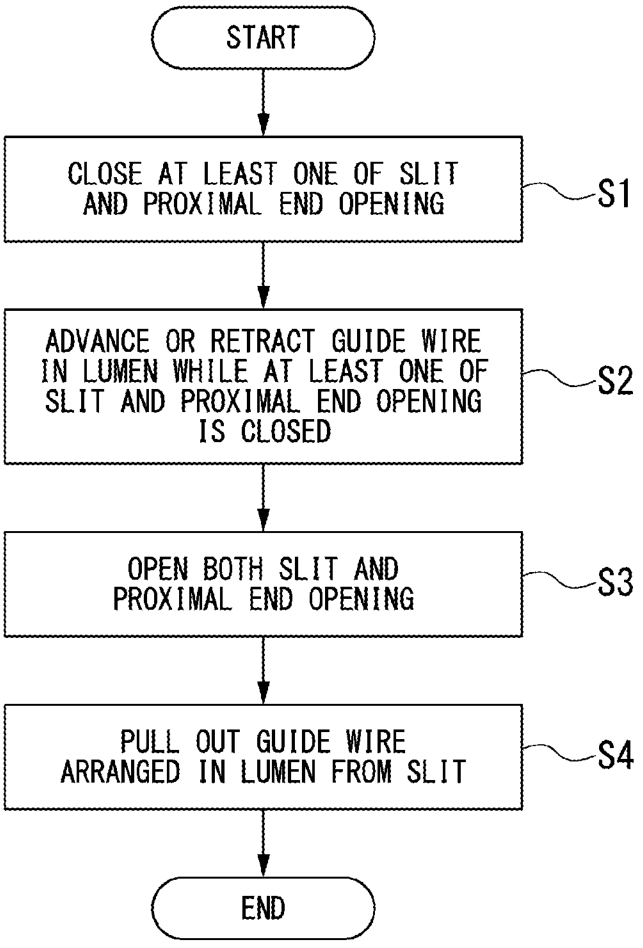
FIG. 36 is a flow chart showing a method for using the treatment tool for an endoscope.

Next, a method for using the treatment tool 1 will be described with reference to FIGS. 9, 10, and 36. The sheath 2 is inserted into the forceps plug 104 and inserted through the treatment tool channel 105, and the treatment tool 1 is protruded from a distal end portion of the endoscope insertion portion 101. The distal end portion of the sheath 2 is bendable along with a curvature of the active bending portion 107. As shown in FIG. 1, the distal end of the sheath 2 is configured to be further bendable by the elevator.

Figure 9:
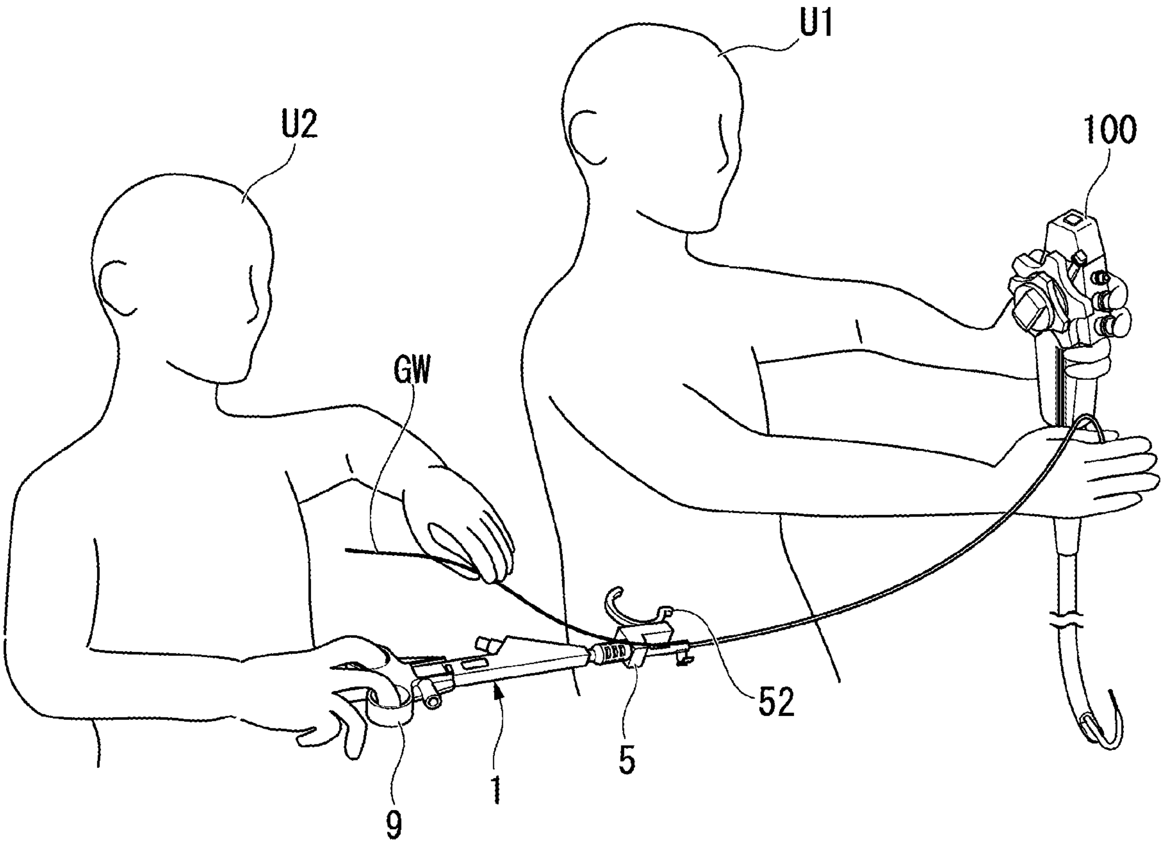
FIG. 9 is a schematic view showing a usage of the treatment tool for an endoscope according to the first embodiment.
Figure 10:
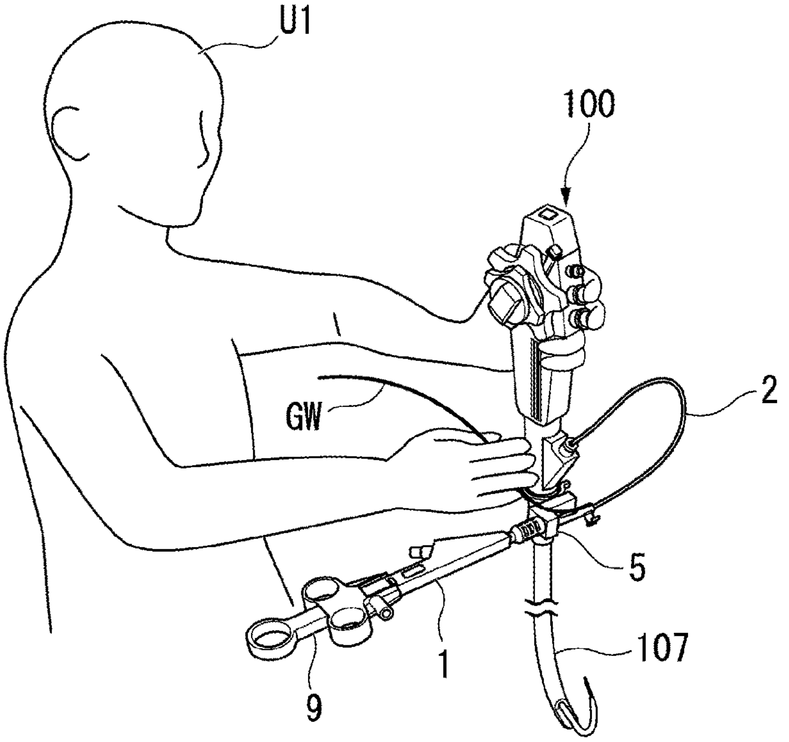
FIG. 10 is a schematic view showing a usage of the treatment tool for an endoscope according to the first embodiment.

FIGS. 9 and 10 show the usage of the treatment tool 1. There are cases of both the treatment tool 1 being used by two operators U1 and U2 as shown in FIG. 9 and the treatment tool 1 being used by one operator U1 as shown in FIG. 10. When the treatment tool 1 is used by two operator U1 and U2, as shown in FIG. 9, an engagement of the hook 52 to the endoscope device 100 is released. The operator U1 holds and operates the endoscope device 100. The operator U2 holds the operation portion 9 and operates the treatment tool 1. The operator U2 holds the guide wire GW and performs an operation of holding a position of the guide wire GW and an operation of advancing and retracting the guide wire GW in accordance with the treatment being performed. As shown in FIG. 10, in a case of operation by only the operator U1, a position of the treatment tool 1 with respect to the endoscope device 100 is held by locking the hook 52 to the grip portion 102 of the endoscope insertion portion 101, and the operator U1 performs all of the operations of the endoscope device 100 and the treatment tool 1 alone. Two operator U1 and U2 operating the treatment tool 1 hold the guide wire GW, and perform an operation for holding the position of the guide wire GW and operations for retracting and advancing the guide wire GW.

First, at least one of the sheath slit 23 and the distal end of the proximal end opening 22 is closed by the suppress portion (first step S1). The guide wire GW is inserted into the guide wire insertion port 55. The distal end of the guide wire GW protrudes from the distal end opening 24 of the sheath 2 and is inserted into the hollow organ.

Next, the guide wire GW advances or retracts in the lumen 21 while closing at least one of the sheath slit 23 of the sheath 2 and the distal end of the proximal end opening 22 (step S2). That is, the guide wire GW advances in the first state. A proximal end portion of the guide wire GW is drawn out from the proximal end opening 22 of the sheath 2 and the guide wire insertion port 55, and is exposed and elongated outside the sheath 2. The guide wire GW is inserted into the guide wire lumen 21 so as to be advanceable and retractable. Accordingly, when the operator advances or retracts the guide wire GW drawn out from the guide wire port 55, the guide wire GW advances or retracts in the guide wire lumen 21.

There is a case that an advancing and retracting action of the guide wire GW cannot be smoothly performed due to a state of the sheath 2, such as a curvature state of the sheath 2 being inserted into the body, or a case of contrast medium remaining in the lumen 29 after injecting the contrast medium. In this state, if the operator operating the guide wire GW advances the guide wire GW, although a force in a direction that the guide wire GW is pushed into the guide wire lumen 21 is applied to the proximal region of the guide wire GW, the guide wire GW does not advance smoothly. As a result, the guide wire GW is bent at an outside of the guide wire insertion port 55. If the guide wire GW is continuously pushed in this state, the guide wire GW moves to a direction entering the slit 56 and the sheath slit 23 from the distal end 551 of the guide wire insertion port 55. If the guide wire GW is exposed to the outside of the guide wire lumen 21 at a further distal side D than the proximal portion of the slit, it takes time to return the guide wire GW to an inside of the guide wire insertion port 55. However, in the embodiment, the suppressor 7 covers the slit 56 to close the slit 56 when the suppressor 7 is arranged in the first state. Accordingly, the suppressor 7 prevents the guide wire GW from entering the slit 56 at the coupling portion 5 side. As a result, if the operator advances the guide wire GW when the suppressor 7 is in the first state, it is possible to prevent the guide wire GW entering the slit 56 against the second operator's will.

After the second step S2, both the proximal end of the sheath slit 23 and the distal end of the proximal end opening 22 are opened (third step S3). That is, the suppressor 7 is switched to the second state. For example, when replacing with a knife wire after injection of a contrast medium, or the like, there is a case in which the sheath 2 is removed from the endoscope insertion portion 101 while the guide wire GW remains indwelled in the body. At the time of this operation, as shown in FIG. 3, the operator of the treatment tool 1 rotates the suppressor 7 while gripping the grip projection 72 such that the cover main body 71 does not cover the slit 56 to switch the suppressor 7 to the second state.

Next, the guide wire GW is inserted into the slit 66 and the sheath slit 23. The sheath 2 is exposed while the guide wire GW remains indwelled in the body, and the treatment tool 1 is removed from the endoscope insertion portion 101 (fourth step S4). The fourth step will be explained in detail. First, the guide wire GW is continuously inserted into the slit 56 and the sheath slit 23, and the guide wire GW pulled out from the proximal end opening 22 of the sheath 2 is moved toward the vicinity of the forceps plug 104 of the endoscope device 100. When the guide wire GW, which is pulled out, is moved to the vicinity of the forceps plug 104, the guide wire GW is fixed to the endoscope device 100 at the vicinity of the forceps plug 104. After that, the guide wire GW is kept fixed in the vicinity of the forceps plug 104, and the base portion 4, i.e., the treatment tool 1 is pulled toward the proximal side P. When the treatment tool 1 is used in a state in which the hook 52 is engaged with the grip portion 102, the hook 52 is pulled toward the proximal side P after releasing the engagement of the hook 52 with the grip portion 102. At this time, the position where the guide wire GW is pulled out moves toward the distal end side of the sheath slit 23. When the treatment tool 1 is pulled out from the treatment tool channel 105 and the position where the guide wire GW is pulled out moves to the distal end of the sheath slit 23, that is, when the distal end of the sheath slit 23 moves to the vicinity of the forceps plug 104, a withdrawing operation is temporarily stopped, and the fixation of the guide wire GW to the vicinity of the forceps plug 104 is released. After releasing the fixation of the guide wire GW, only the treatment tool 1 is further pulled out from the treatment tool channel 105 while holding the guide wire GW so as not to move with respect to the endoscope device 100. When the distal end of the sheath 2 is completely pulled out from the forceps plug 104, the guide wire GW is fixed to the vicinity of the forceps plug 104 again, and the treatment tool 1 is completely pulled out from the guide wire GW.

According to the treatment tool 1 and the method for using the treatment tool according to the present embodiment, when operating the guide wire GW to advance with respect to the sheath 2, the guide wire GW is prevented from entering the slit 56 and the sheath slit 23, and the guide wire GW is capable of smoothly advancing with respect to the sheath 2.

Since the suppressor 7 is configured to be switchable between the first state and the second state, the suppressor 7 is switched to the second state when removing the sheath 2 from the endoscope insertion portion 101, thereby the sheath 2 is smoothly removed while maintaining the state in which the guide wire GW is kept inserted in the body. As a result, shortening of the operation time is achieved.

Figure 11:
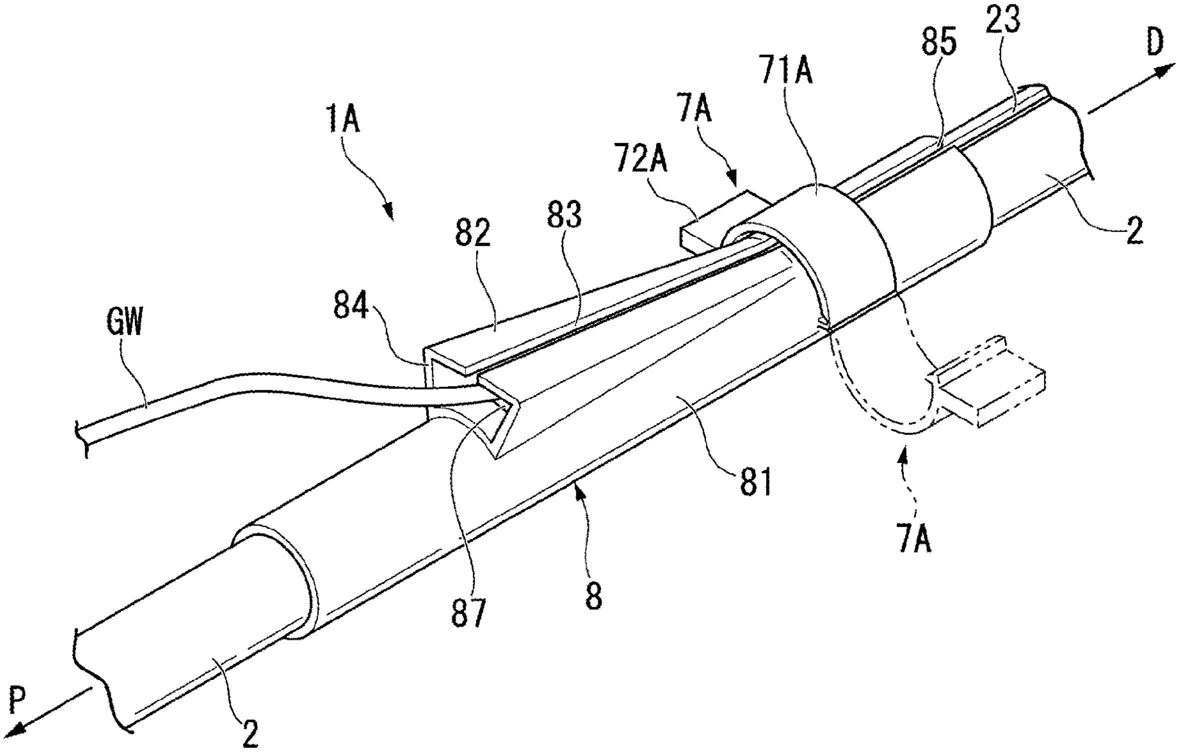
FIG. 11 is a perspective view showing a part of the treatment tool for an endoscope of the modified example of the first embodiment.
Figure 12:
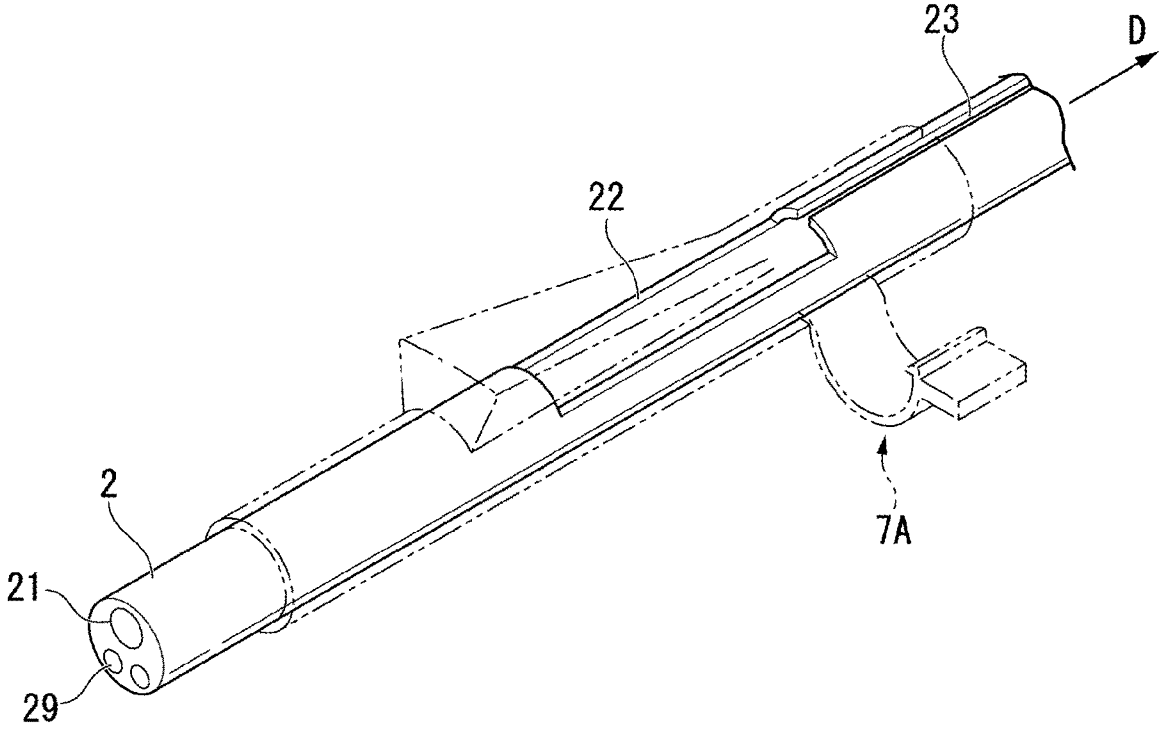
FIG. 12 is a perspective view showing a part of the treatment tool for an endoscope of FIG. 11.
Figure 13:
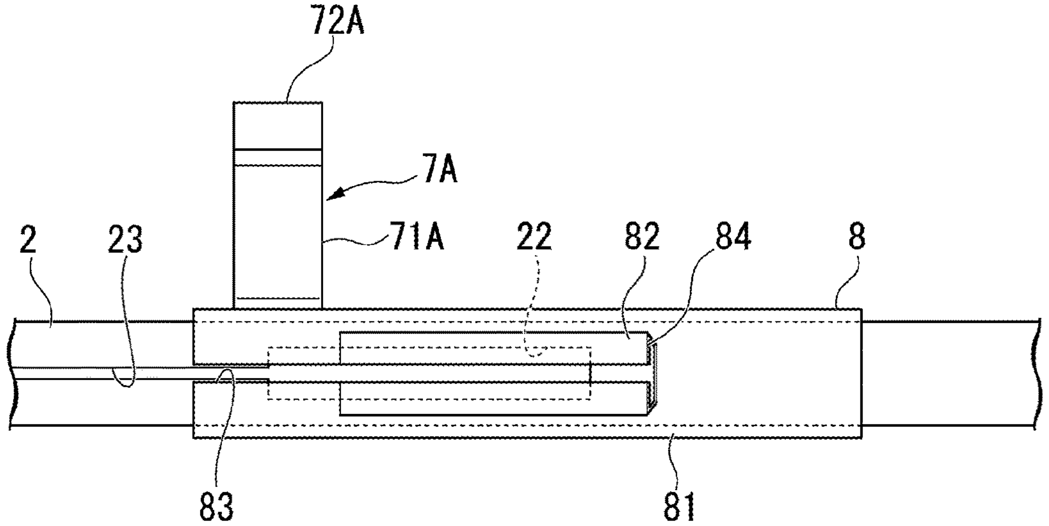
FIG. 13 is a side view showing a part of the treatment tool for an endoscope of FIG. 11.

The aspect of the treatment tool 1 is not limited to the above embodiment. FIGS. 11 to 13 show a modified example of a treatment tool 1A. In the following descriptions, the same components as those already described are denoted by the same reference numerals, and repeated descriptions will be omitted. In the modified example shown in FIGS. 11 to 13, the configuration of the coupling portion is different from that of the above embodiment. The coupling portion 5 of the treatment tool 1 is not limited to the configuration example of the first embodiment. For example, the hook 52 is not an essential element. The sheath 2 may be inserted into a funnel tube 8 and the guide wire GW may be pulled out of the sheath 2 as in the treatment tool 1A of the modified example.

The funnel tube 8 includes a cylinder body 81, a funnel portion 82, and a suppressor 7A. A sheath inserting passage that penetrates the cylinder body 81 in the longitudinal axis direction is formed in the cylinder body 81, and the sheath 2 is inserted into the inserting passage. The funnel portion 82 is provided to protrude from the outer surface of an intermediate portion in the longitudinal direction of the cylinder body 81.

Each of slits 83 and 85 is formed in the cylinder body 81 and the funnel portion 82. The slits 83 and 85 and the sheath alit 23 of the sheath 2 are provided at the same circumferential position. Inside of the funnel portion 82, an opening 87 is formed on a side surface of the cylinder body 81. The opening 87 on the side surface of the cylinder body 81 is provided at a position corresponding to the proximal end opening 22 of the sheath 2. The opening 87 on the side surface of the cylinder body 81 communicates with the guide wire lumen 21 of the sheath 2 via the proximal end opening 22.

A suppressor 7A is provided on the cylinder body 81 on the distal side D from the funnel portion 82. As shown in FIGS. 12 and 13, the suppressor 7A is provided at a position covering the proximal end of the sheath slit 23 and the distal end of the proximal end opening 22 of the sheath 2 inserted into the cylinder body 81. The suppressor 7A is rotatably coupled to the cylinder body 81. The suppressor 7A is configured to be switchable between a first state in which a cover body 71A covers the slit 85 and a second state in which the cover body 71A opens the slit 85. The suppressor 7A rotates about the coupling portion between the fixing portion 79 and the funnel tube 8, the same as the suppressor 7 of the first embodiment.

The guide wire GW is passed through the funnel portion 82 from the guide wire lumen 21 of the sheath 2 via an opening on a side surface of the cylinder body 81. The guide wire GW is drawn out to the treatment tool 1 from a proximal opening 84 of the funnel portion 82.

When the guide wire GW is made to advance while the suppressor 7A is in the first state, if the distal region of the guide wire GW does not advance even if the operator of the treatment tool 1 advances the guide wire GW, the suppressor 7A prevents the guide wire GW from entering the distal side D from the distal end of the slit 85. As a result, the guide wire GW is prevented from entering the distal side D from the proximal end of the sheath slit 23.

On the other hand, when the treatment tool 1A is removed from the endoscope insertion portion 101 while the guide wire GW remains indwelled in the body, the suppressor 7A is operated to be rotated to switch to the second state. After that, the second operator operates the guide wire GW to enter the slit 83 from the proximal opening 84 of the funnel portion 82, and goes through to the slit 85. In this state, when the funnel tube 8 is pulled toward the proximal side P, the guide wire GW enters the sheath slit 23 and the guide wire GW is pulled out of the sheath 2 from the guide wire lumen 21.

The same as in the first embodiment, the treatment tool 1A of the modified example prevents the guide wire GW from entering the sheath slit 23 when the guide wire GW is advanced and retracted with respect to the sheath 2, and smoothly advances the guide wire GW relative to the sheath 2.

Since the suppressor 7A is configured to be switchable between the first state and the second state, when the sheath 2 is withdrawn from the endoscope insertion portion 101, the suppressor 7A is switched to the second state, thereby the sheath 2 is smoothly removed while maintaining the state where the guide wire GW is inserted into the body. As a result, shortening of the operation time is achieved.

Second Embodiment

Figure 14:
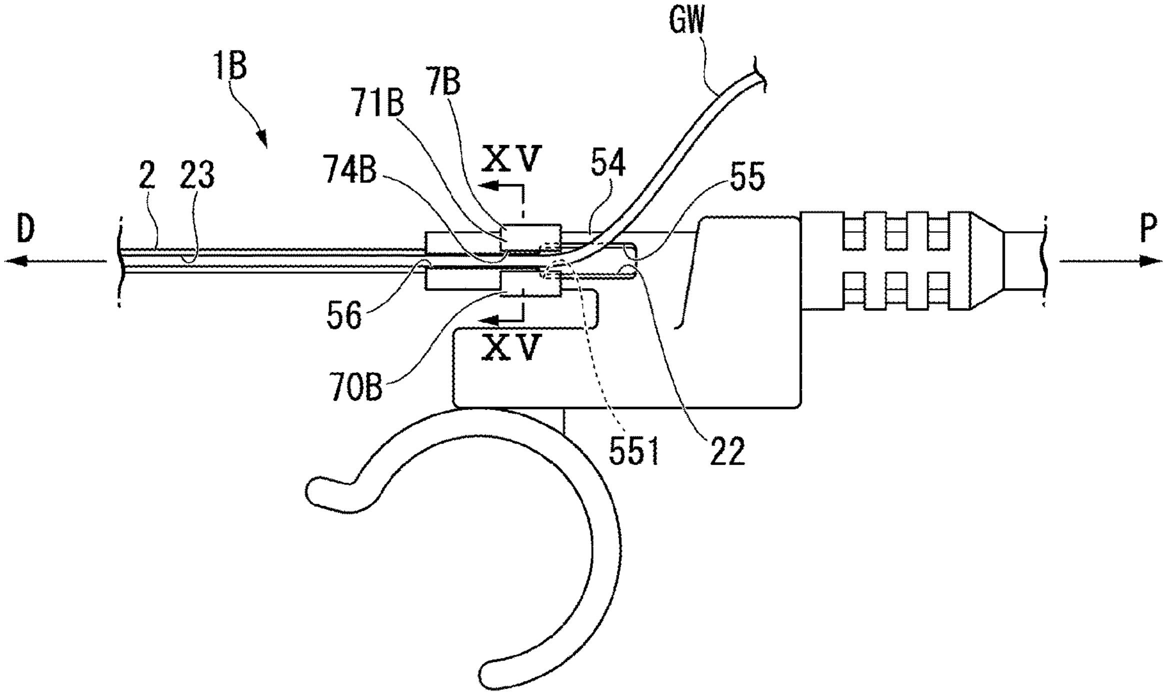
FIG. 14 is a side view showing a part of the treatment tool for an endoscope according to a second embodiment.
Figure 15:
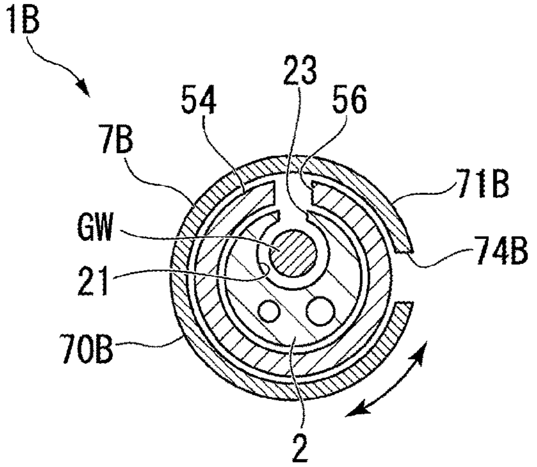
FIG. 15 is a cross-sectional view taken along line XV-XV of FIG. 14.
Figure 16:
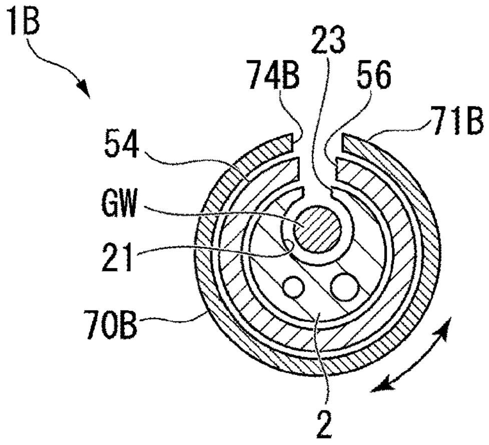
FIG. 16 is a cross-sectional view taken along line XV-XV of FIG. 14 showing a suppression portion in a second state.

A second embodiment according to a treatment tool 1B will be described with reference to FIGS. 14 to 16. The treatment tool 1B according to the second embodiment is an example in which the configuration of a suppressor 7B is different from that of the first embodiment. The suppressor 7B is provided to the sheath coupling portion 54 so as to be rotatable with respect to the sheath coupling portion 54. FIG. 15 is a cross-sectional view taken along line XV-XV of FIG. 14, and shows the suppressor 7B in the first state. FIG. 16 is a cross-sectional view taken along line XV-XV of FIG. 14, and shows the suppressor 7B in the second state. As shown in FIGS. 15 and 16, the suppressor 7B is a member having a substantially C-shaped in a cross section perpendicular to the longitudinal axis. The suppressor 7B is mounted on an outer surface of the sheath coupling portion 54 having a circular shape in a cross section perpendicular to the longitudinal axis so as to be rotatable in the circumferential of direction. FIG. 15 shows a cross-sectional view of the suppressor 7B in the first state. FIG. 16 shows a cross-sectional view of the suppressor 7B in the second state.

The suppressor 7B has a slit 74B. The slit 74B is a slit having an opening width equal to or slightly wider than those of the sheath slit 23 and the slit 56. As shown in FIG. 16, in the second state, the slit 74B of the suppressor 7B is arranged at a position substantially the same as the sheath slit 23 and the slit 56 of the sheath coupling portion 54 in the circumferential direction. As shown in FIG. 15, when the suppressor 7B is arranged in the first state, the sheath slit 23 and the slit 56 of the sheath coupling portion 54 are covered with the suppressor 7B.

In the present embodiment, the suppressor 7B may be configured to be switchable between the first state and the second state by rotating the suppressor 7B relative to the sheath coupling portion 54.

According to the treatment tool 1B of the present embodiment, the same as the first embodiment, when operating the guide wire GW to advance and retract with respect to the sheath 2, the guide wire GW is prevented from entering the slit 56 and the sheath slit 23, and the guide wire GW is capable of being smoothly advanced with respect to the sheath 2.

Since the suppressor 7B is configured to be switchable between the first state and the second state, the suppressor 7B is rotated to switch to the second state when removing the sheath 2 from the endoscope insertion portion 101, thereby the sheath 2 is smoothly removed while maintaining the state in which the guide wire GW is kept inserted in the body. As a result, shortening of the operation time is achieved.

Figure 17:
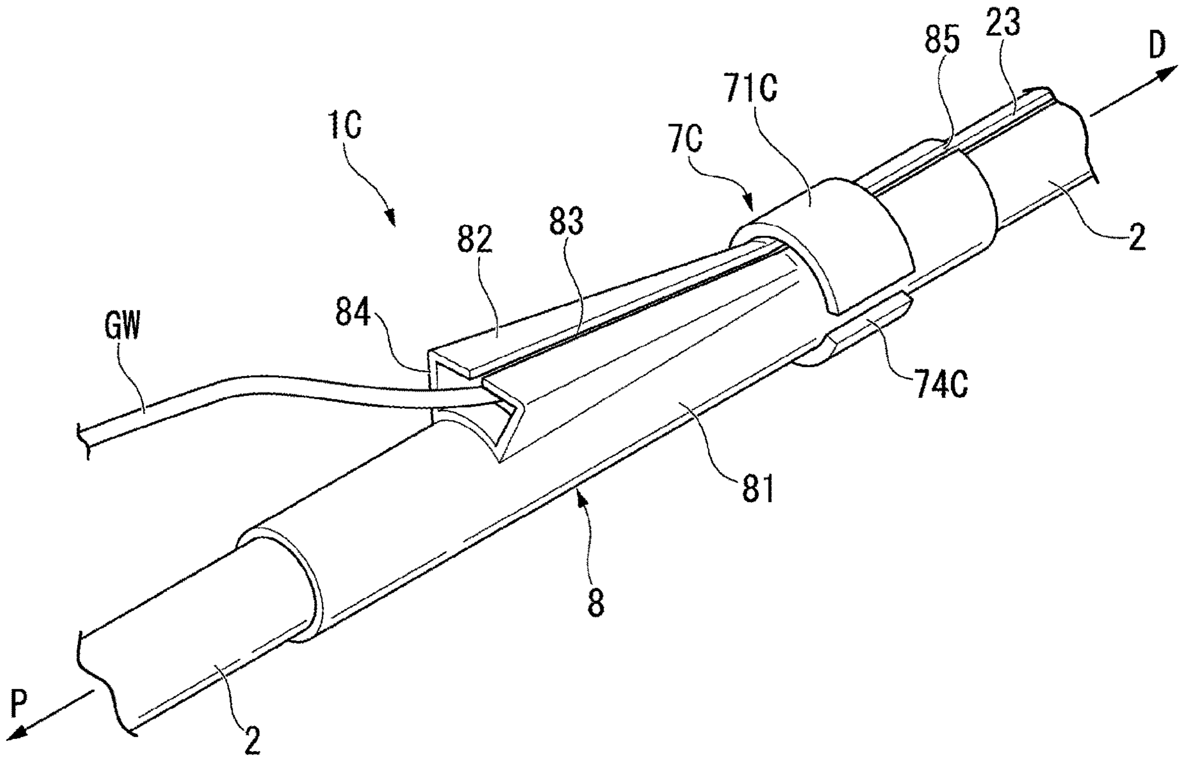
FIG. 17 is a perspective view showing a part of the treatment tool for an endoscope of the modified example of the second embodiment.
Figure 18:
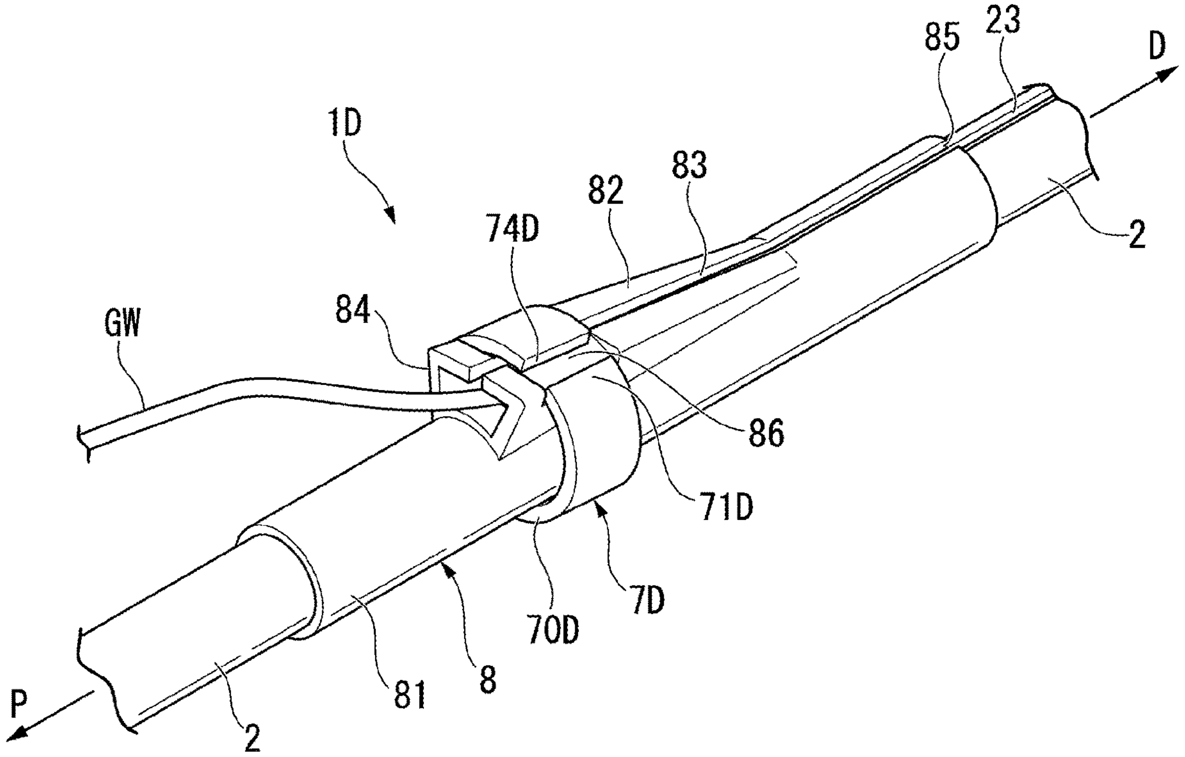
FIG. 18 is a perspective view showing a part of the treatment tool for an endoscope of the modified example of the second embodiment.
Figure 19:
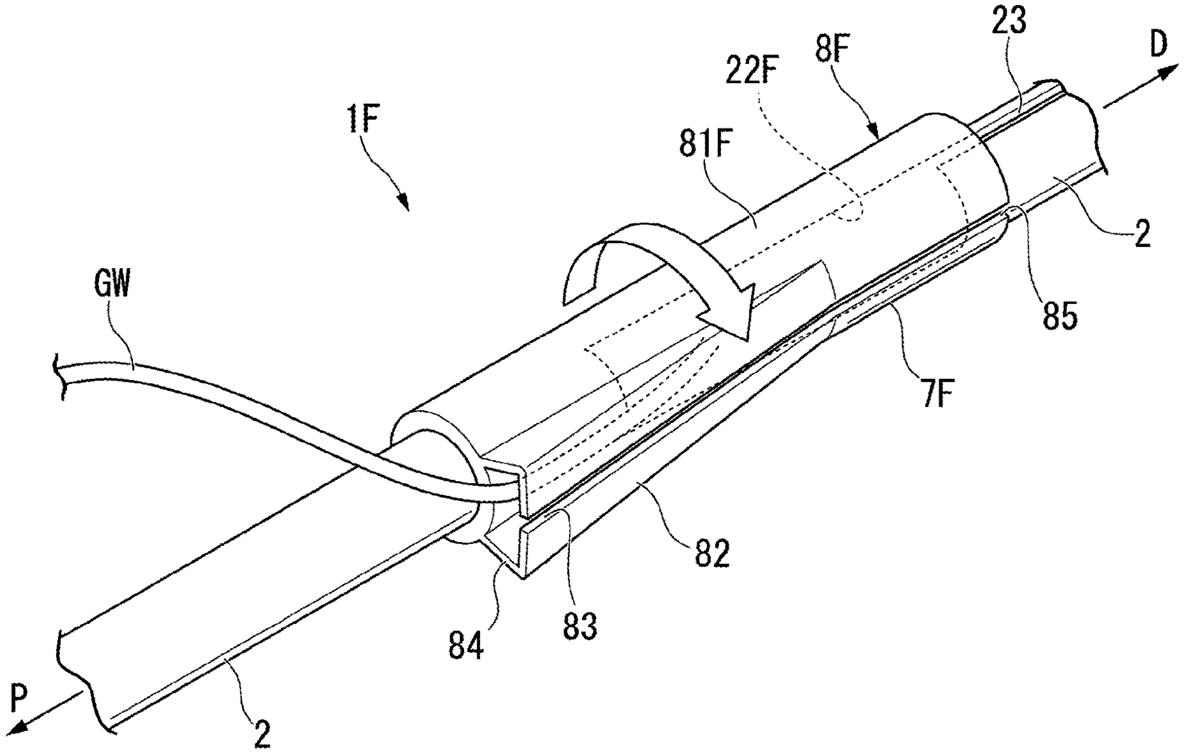
FIG. 19 is a perspective view showing a part of the treatment tool for an endoscope of the modified example of the second embodiment.

The aspect of the treatment tool is not limited to the above described aspect. FIGS. 17 to 19 show modified examples of treatment tools 1C, 1D, and 1F. The treatment tool 1C of a modified example shown in FIG. 17 includes the funnel tube 8, the same as the example of FIG. 11. A suppressor 7C is provided on the distal end portion of the funnel tube 8. The suppressor 7C has the same configuration as in the second embodiment. The suppressor 7C is rotatably attached to the funnel tube 8. FIG. 17 shows the suppressor 7C in the first state. As shown in FIG. 17, in the first state, the sheath slit 23 and the slit 85 of the cylinder body 81 are covered with the suppressor 7C. When the suppressor 7B is arranged in the second state, a slit 74C of the suppressor 7C is arranged at a position substantially equal to the sheath slit 23 and the slit 85 of the cylinder body 81 in the circumferential direction. As a result, the guide wire GW is capable of passing through the slit 83 of the funnel portion 82 and entering the slit 85 of the cylinder body 81 and the sheath slit 23, and the treatment tool 1C is capable of being removed while the guide wire GW is indwelled.

The treatment tool 1D of the modified example shown in FIG. 18 differs from the treatment tool 1C of the modified example of FIG. 17 in the position of a suppressor 7D. The treatment tool 1D of the modified example is provided with the suppressor 7D at the proximal portion of the funnel portion 82. The funnel portion 82 is formed with a locking groove 86 in which the suppressor 7D is locked. The locking groove 86 is formed along the size and shape of the suppressor 7D. The suppressor 7D is arranged in the locking groove 86 and is rotatable in the locking groove 86 in the circumferential direction. The suppressor 7D is switched between the first state and the second state by rotating in the locking groove 86 in the circumferential direction. FIG. 18 shows the suppressor 7D in the first state. In the first state, a part of the proximal portion of the slit 83 of the funnel portion 82 is covered with the suppressor 7D. When a part of the proximal portion of the slit 83 of the funnel portion 82 is covered with the suppressor 7D, the guide wire GW is prevented from entering the distal side D of the slit 83. Since the suppressor 7D is provided on the more proximal side P than the proximal portion of the sheath slit 23, the guide wire GW is prevented from entering the sheath slit 23. When the suppressor 7D is rotated by the operator and arranged in the second state, the slits 83 of the funnel portion 82 and slits 74D of the suppressor 7D are arranged at substantially the same position in the circumferential direction. The guide wire GW is capable of passing through the slit 83 of the funnel portion 82 and entering the slit 85 of the cylinder body 81 and the sheath slit 23. As a result, the treatment tool 1C is capable of being removed while the guide wire GW is indwelled.

The treatment tool 1F of a modified example shown in FIG. 19 is an example in which a funnel tube 8F is rotatably provided with respect to the sheath 2 and functions as a suppressor 7F. FIG. 19 shows the suppressor 7F in the first state. When the operator rotates the funnel tube 8 with respect to the sheath 2 about the central axis, the suppressor 7F is capable of being switched between the first state and the second state. The sheath 2 is formed with a guide wire insertion opening 22F elongated in the circumferential direction. A through-hole that communicates with the guide wire insertion port 22F and the funnel portion 82 is formed in a cylinder body 81F of the funnel tube 8F. When the suppressor 7F is in both the first state and the second state, the guide wire insertion port 22F and the through-hole are communicated with each other, and the guide wire GW is configured to advance and retract. In the first state, the guide wire GW is restricted from entering the sheath slit 23. When the operator rotates the funnel tube 8F to place it in the second state, the slit 83 of the funnel portion 82, the slit 74D of the suppressor 7D, and the sheath slit 23 are arranged at substantially the same circumferential positions. As a result, the guide wire GW is capable of passing through the slit 83 of the funnel portion 82 and entering the slit 85 of the cylinder body 81 and the sheath slit 23, and the treatment tool 1C is capable of being removed while the guide wire GW is indwelled.

According to the treatment tools 1C, 1D, and 1F of the modified examples shown in FIGS. 17 to 19, similarly to the treatment tool 1B according to the second embodiment, when the guide wire GW is advanced and retracted with respect to the sheath 2, the guide wire GW is prevented from entering the slit 85 and the sheath slit 23, and the guide wire GW is smoothly advanced with respect to the sheath 2.

Since the suppressors 7C, 7D, and 7F are configured to be switchable between the first state and the second state, the suppressors 7C, 7D, and 7F are rotated to switch to the second state when removing the sheath 2 from the endoscope insertion portion 101, thereby, the sheath 2 is smoothly removed while maintaining the state in which the guide wire GW is kept inserted in the body. As a result, shortening of the operation time is achieved.

Third Embodiment

A treatment tool 1G according to the third embodiment will be described with reference to FIGS. 20 to 22. The treatment tool 1G according to the third embodiment is an example in which the configuration of a suppressor 7G is different from that of the first embodiment. As shown in FIGS. 21 and 22, a cover body 71G of the suppressor 7G is provided at a position covering the slit 56 of the sheath coupling portion 54 and a distal end 551G of the guidewire insertion port 55.

Figure 20:
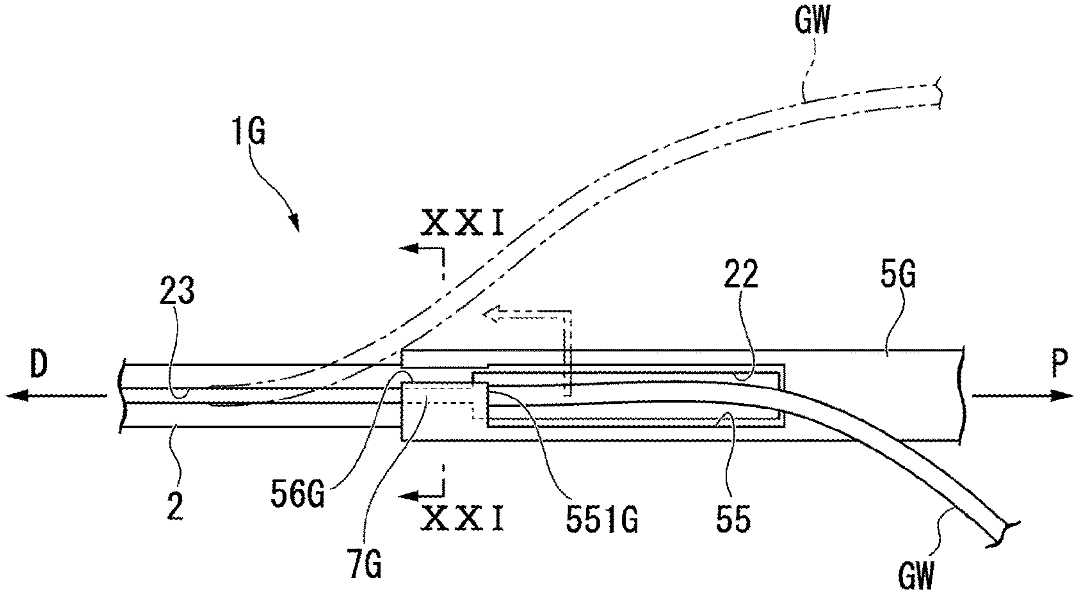
FIG. 20 is a side view showing the treatment tool for an endoscope of a third embodiment.
Figure 21:
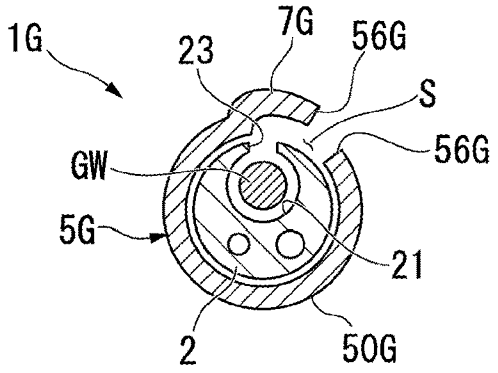
FIG. 21 is a cross-sectional view taken along line XXI-XXI of FIG. 20.
Figure 22:
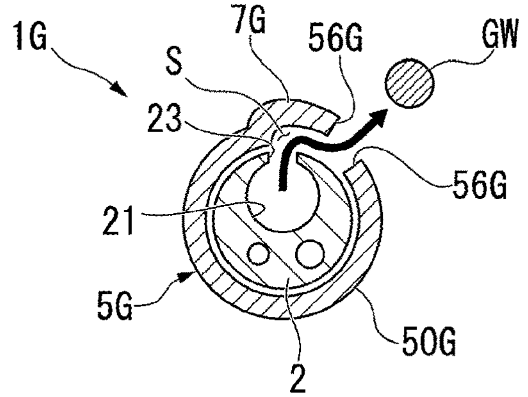
FIG. 22 is a cross-sectional view taken along line XXI-XXI of FIG. 20.

FIGS. 21 and 22 are cross-sectional views taken along line XXI-XXI of FIG. 20. As shown in FIGS. 21 and 22, a coupling portion 5G has a tubular shape, and the proximal portion of the sheath 2 is inserted into the coupling portion 5G. The guide wire insertion port 55 is opened in the coupling portion 5G. A slit 56G is formed from the distal end 551G of the guide wire insertion port 55 to the distal end of the coupling portion 5G.

The suppressor 7G is provided so as to cover the sheath slit 23 at a position spaced radially outward from the sheath slit 23. The suppressor 7G is separated from the outer peripheral surface of the sheath 2 such that the guide wire GW is movable from the sheath slit 23 to the slit 56G. The slit 560 of the coupling portion 5G is provided at a position offset from the position of the sheath slit 23 in the circumferential direction. That is, the suppressor 7G is formed with the slit 56G opening at a position different from the opening position of the sheath slit 23 in the circumferential direction of the sheath 2.

As shown in FIG. 22, the guide wire GW taken out from the sheath slit 23 is configured to pass through the gap S inside the suppressor 7G and to be taken out from the slit 56G. If the distal region of the guidewire GW does not advance when the operator performs an operation to advance the guidewire GW, the guidewire GW moves within the guidewire insertion port 55 radially outward of the coupling portion 5G. At this time, since the distal end 5510 of the guidewire insertion port 55 is covered with the suppressor 7G, the guidewire GW contacts the distal end 551G of the guidewire insertion port 55, and is prevented from entering the slit 56G of the coupling portion 5G and the sheath slit 23. On the other hand, when the operator wishes to remove the guide wire GW from the guide wire lumen 21, as indicated by the two-dot chain line in FIG. 20, the operator lifts the guide wire GW radially outward of the sheath 2 and pulls it in the circumferential direction. As shown in FIG. 22, the guide wire GW passes from the sheath slit 23 through the gap S inside the suppressor 7G and is exposed to the outside of the suppressor 7G through the slit 560. That is, the guide wire GW is capable of entering the distal side D of the slit 56G avoiding the suppressor 7G. As a result, the sheath 2 is smoothly removed while maintaining the state in which the guide wire GW is kept inserted in the body, thereby shortening the operation time.

According to the treatment tool 1G of the present embodiment, when the guide wire GW is advanced and retracted with respect to the sheath 2, the guide wire GW is prevented from entering the slit 56G and the sheath slit 23, and the guide wire GW is smoothly advanced relative to the sheath 2.

Figure 23:
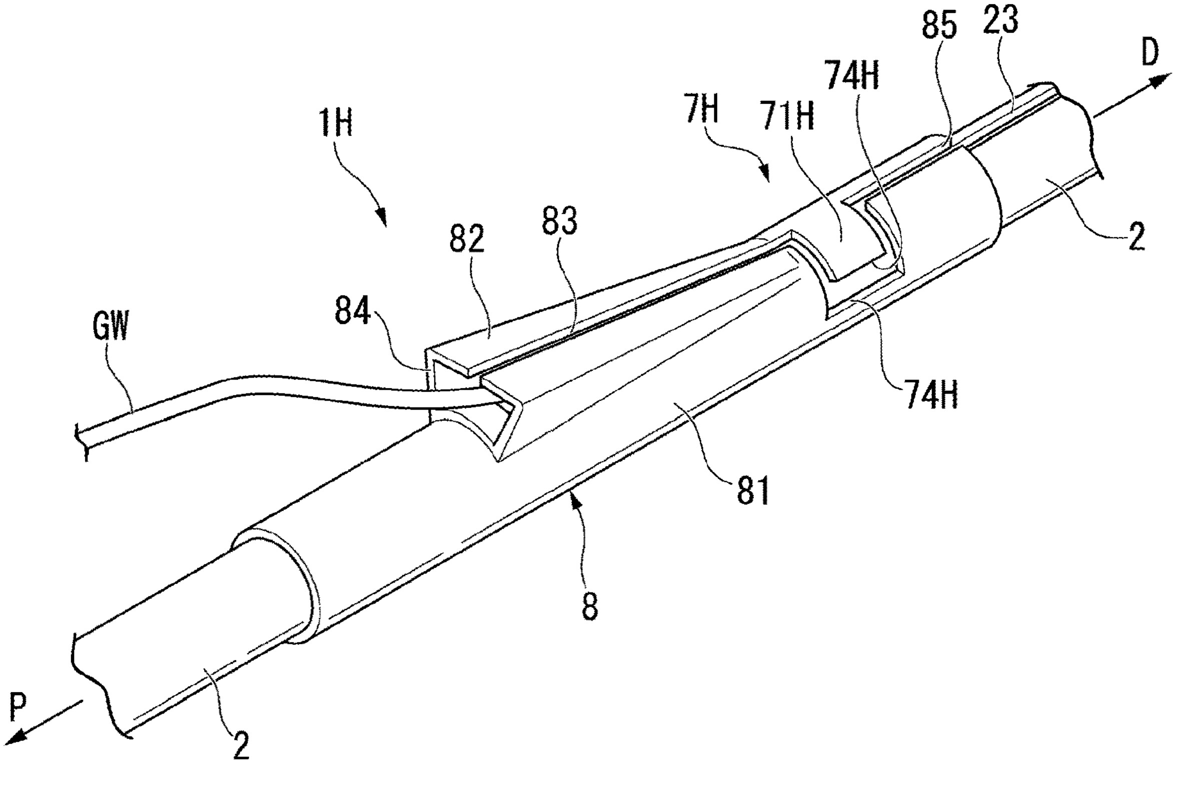
FIG. 23 is a perspective view showing a part of the treatment tool for an endoscope of the modified example of the third embodiment.

FIG. 23 shows a treatment tool 1H as a modified example of the third embodiment. The treatment tool 1H of the modified example shown in FIG. 23 differs from the above-described embodiment in the configuration of the coupling portion. For example, the configuration of the suppressor 7G of the third embodiment may also be applied to the funnel tube 8. In the treatment tool 1H of this modified example, a suppressor 7H (plate-shaped suppressor) is formed integrally with the distal portion of the cylinder body 81 of the funnel tube 8. The plate-shaped suppressor 7H is provided between the slit 83 of the funnel portion 82 and the slit 85 of the cylindrical body 81. As shown in FIG. 23, the suppressor 7H extends along the circumferential direction of the cylinder body 81 at a position intersecting the slit 85 of the cylinder body 81 on the distal aide D from the funnel portion 82. A slit 74H is formed around the suppressor 7H. The slit 74H is formed to be bent. The slit 74H communicates with the slit 83 of the funnel portion 82 and the slit 85 of the cylinder body 81. The same as the third embodiment, the suppressor 7H is spaced radially outward from the sheath 2 and provided at a position covering the sheath slit 23.

Due to a cover body 71H provided in the treatment tool 1H, the guide wire GW is prevented from entering the sheath slit 23 when the guide wire GW moves toward the distal side D from the slit 83 of the funnel portion 82 against the intention of the operator. On the other hand, when the guide wire GW is to be removed from the guide wire lumen 21, the guide wire GW is inserted into the slit 83 of the funnel portion 82, and pulled out to expose the guide wire GW to the suppressor 7H. After that, if the guide wire GW is moved in the circumferential direction of the sheath 2 along the slit 74H, the guide wire GW is exposed to the outside of the funnel tube 8 from the slit 74H through the gap S inside the suppressor 7H, the same as the treatment tool 1G.

According to the treatment tool 1H, when the guide wire GW is advanced and retracted with respect to the sheath 2, the guide wire GW is prevented from entering the distal end of the slit 85 and the sheath slit 23, and the guide wire GW is smoothly advanced with respect to the sheath 2. On the other hand, according to the treatment tool 1H, when the guide wire GW is pulled out from the slit 74H of the suppressor 7H, the guide wire GW is capable of entering the sheath slit 23, and the guide wire GW is capable of being removed from the guide wire lumen 21 of the sheath 2.

Fourth Embodiment

A treatment tool 1I according to the fourth embodiment will be described with reference to FIGS. 24 to 26. The treatment tool 1I according to the fourth embodiment is an example in which the configuration of a suppressor 7I is different from each of the above-described embodiments. The suppressor 7I is provided at the distal portion of the sheath coupling portion 54. The suppressor 7I has a pair of knob pieces 75, a pair of cover main bodies 71I, and a pair of projections 76. A slit 74I is formed along the slit 56 of the sheath coupling portion 54 in the suppressor 7I. The cover body 71I and the knob pieces 75 are integrally formed on both sides of the slit 74I. The suppressor 7I is formed integrally with the sheath coupling portion 54. The cover main body 71I is provided so as to cover the sheath 2 and the sheath coupling portion 54 from above. The knob pieces 75 extend obliquely from the end of the cover main body 71I toward the side of the sheath coupling portion 54 (downward in FIG. 25). The knob pieces 75 are formed continuously with the cover main body 71I. The pair of protrusions 76 are provided on the outer peripheral surface of the sheath coupling portion 54 at positions facing the rear surface of the knob pieces 75. The knob pieces 75 are harder than the cover main body 71I. The cover main body 71I is an example of a cover portion. The knob pieces 75 are an example of a switching member.

Figure 24:
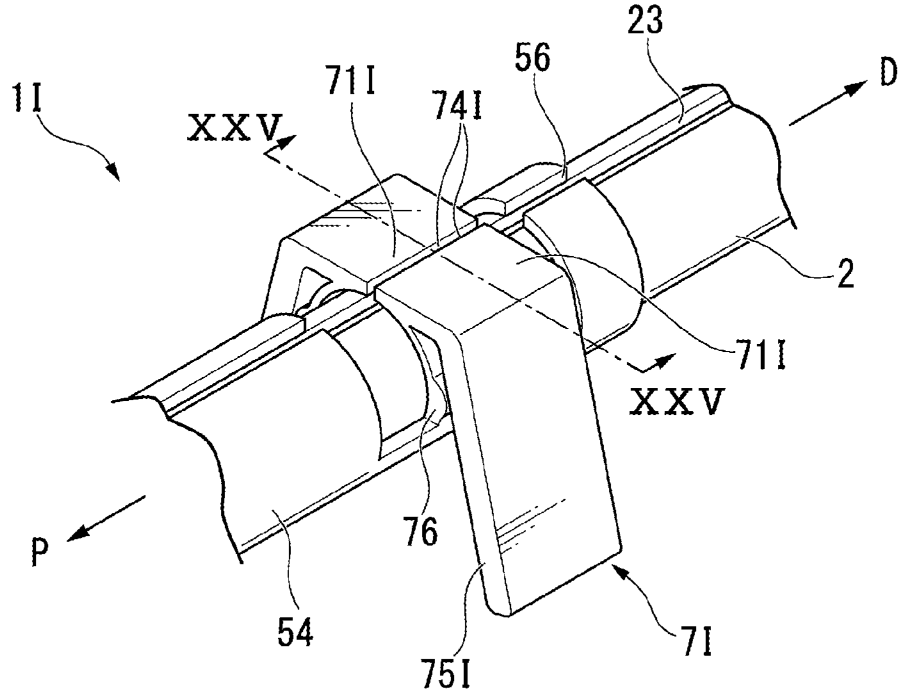
FIG. 24 is a perspective view showing a part of the treatment tool for an endoscope of a fourth embodiment.
Figure 25:
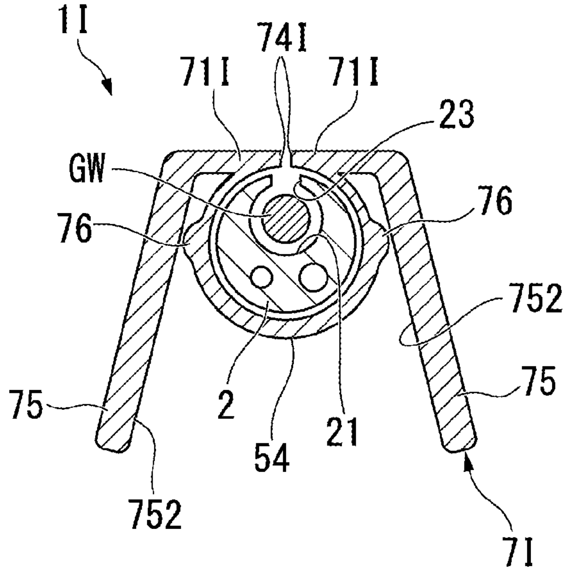
FIG. 25 is a cross-sectional view taken along line XXV-XXV of FIG. 24.
Figure 26:
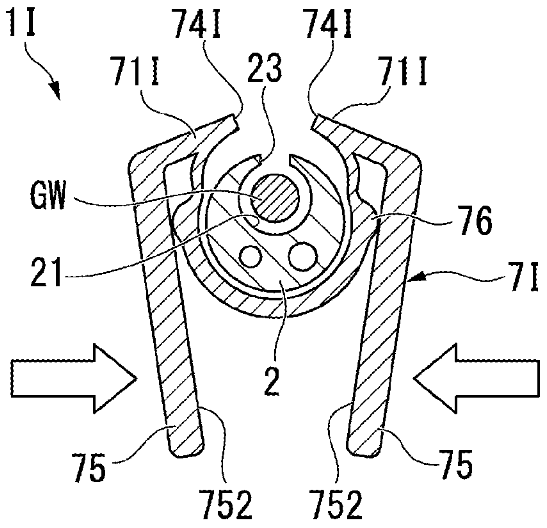
FIG. 26 is a cross-sectional view taken along line XXV-XXV of FIG. 24 showing the suppression portion in the second state.

FIGS. 25 and 26 are ross-sectional views taken along line XXV-XXV of FIG. 24. FIG. 25 shows the suppressor 7I in the first state. FIG. 26 shows the suppressor 7I in the second state. In a natural state in which no external force is applied to the pair of knob pieces 75, as shown in FIG. 25, a pair of cover main bodies 71I are arranged close to each other and the suppressor 7I is in the first state in which the sheath slit 23 is covered. When the suppressor 7I is in the first state, if the distal region of the guidewire GW does not advance even if the operator advances the guidewire GW, the guidewire GW is prevented from entering the sheath slit 23 positioned at the distal side D from the distal end of the slit 56 by the suppressor 7I.

As shown in FIG. 26, when a force is applied in the direction in which the lower ends of the pair of knob pieces 75 approach each other, the rear surface 752 of the knob pieces 75 contacts the projection 76, tilts the cover body 71I, and opens the slit 74I. As a result, the suppressor 7I is in the second state in which the upper portion of the sheath slit 23 is not covered. The knob pieces 75 are provided symmetrically on both sides of the sheath coupling portion 54 across the slit 56. In the second state, when the sheath coupling portion 54 is pulled proximally P, the guide wire GW enters the sheath slit 23 and is pulled out of the sheath 2 from the guide wire lumen 21. The treatment tool 1I is removed from the endoscope insertion portion 101 while keeping a state in which the guide wire GW is indwelled in the body. When an external force applied to the knob pieces 75 is released, the lower ends of the pair of knob pieces 75 move away from each other to restore the first state.

According to the treatment tool 1I in the present embodiment, since the suppressor 7I is configured to be switchable between the first state and the second state, when the sheath 2 is withdrawn from the endoscope insertion portion 101, the suppressor 7A is switched to the second state, thereby the sheath 2 is smoothly removed while maintaining the state where the guide wire GW is inserted into the body. As a result, shortening of the operation time is achieved.

Figure 27:
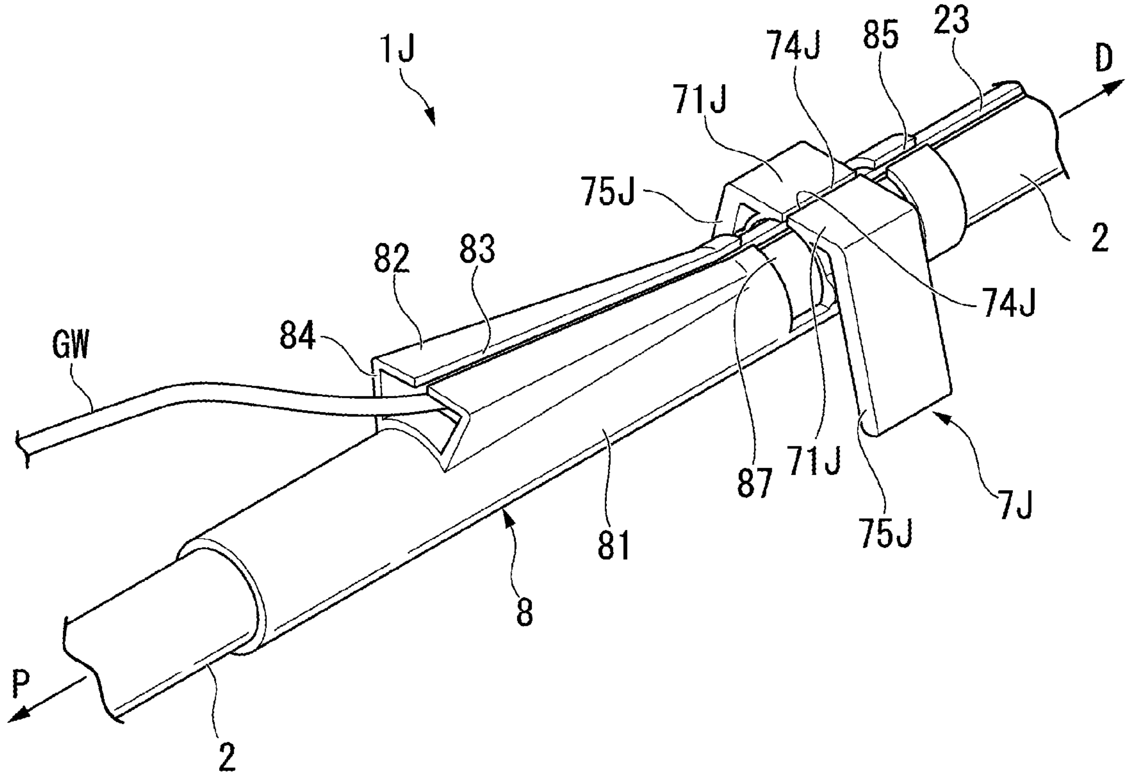
FIG. 27 is a perspective view showing a part of the treatment tool for an endoscope of the modified example of the fourth embodiment.

FIG. 27 shows a treatment tool 1J as a modified example of the fourth embodiment. In the treatment tool 1J of the modified example shown in FIG. 27, the configuration of the coupling portion is different from that of the above embodiment. For example, the configuration of the suppression portion 7I of the fourth embodiment may also be applied to the funnel tube 8. In the treatment tool 1J of this modified example, the distal portion of the funnel tube 8 is provided with a suppressor 7J. The basic configuration of the suppressor 7J is the same as that of the suppressor 7I of the fourth embodiment. The suppressor 7J is arranged at a position covering the proximal end of the sheath slit 23. When the suppressor 7J is in the first state, even if the guide wire GW is exposed to the outside from the slit 83 of the funnel portion 82, the guide wire GW is prevented from entering the distal side D from the distal end of the slit 85 by the suppressor 7A. As a result, it is possible to prevent the guide wire GW from entering from the proximal end of the sheath slit 23.

On the other hand, when the treatment tool 1J is removed from the endoscope insertion portion 101 while keeping the state in which the guide wire GW is indwelled in the body, a pair of knob pieces 75J of the suppressor 7J are pinched to open and close a pair of cover main bodies 71J to switch to the second state. Thereafter, the operator causes the guide wire GW to enter the slit 83 through the proximal opening 84 of the funnel portion 82 and pass through the slit 85. In this state, if the funnel tube 8 is pulled proximally P, the guide wire GW enters the sheath slit 23 and is pulled out of the sheath 2 from the sheath slit 23.

According to the treatment tool 1J of the modified example, since the suppressor 7J is configured to be switchable between the first state and the second state, in the first state, the guide wire GW is prevented from entering the sheath slit 23 against the operator's will. When the sheath 2 is removed from the endoscope insertion portion 101, the suppressor 7J is switched to the second state, whereby the sheath 2 is smoothly removed while maintaining the state in which the guide wire GW is kept inserted in the body. As a result, shortening of the operation time is achieved.

Fifth Embodiment

Figure 28:
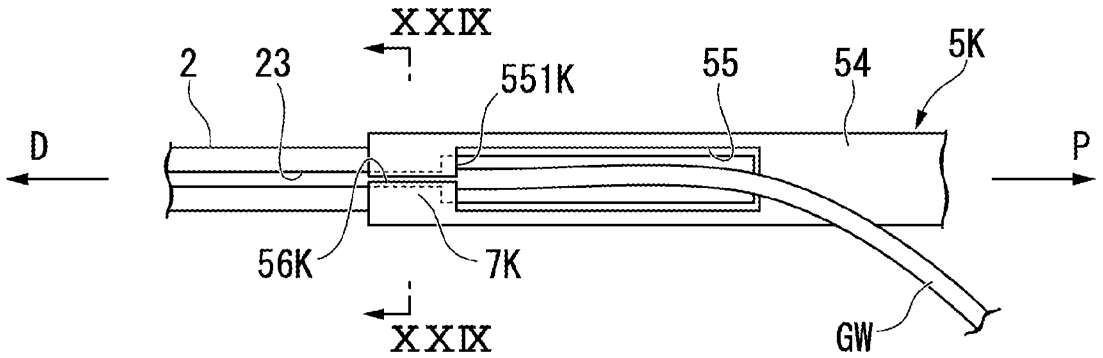
FIG. 28 is a side view showing a part of the treatment tool for an endoscope of the modified example of a fifth embodiment.
Figure 29:
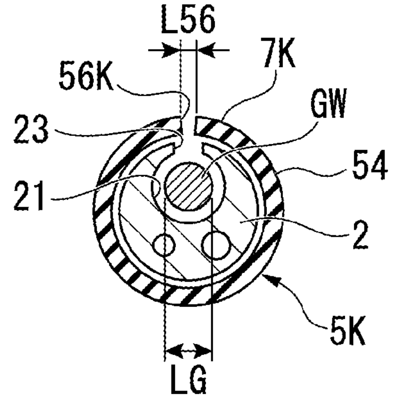
FIG. 29 is a cross-sectional view taken along line XXIX-XXIX of FIG. 28.

A treatment tool 1K according to the fifth embodiment will be described with reference to FIGS. 28 and 29. The treatment tool 1K according to the embodiment differs from the above-described embodiment in the configuration of a suppressor 7K. FIG. 29 is a cross-sectional view taken along line XXIX-XXIX of FIG. 28. A coupling portion 5K has a tubular shape, and the proximal portion of the sheath 2 is inserted therein. The guide wire insertion port 55 is opened in the coupling portion 5K. A slit 56K is formed from a distal end 551K of the guide wire insertion port 55 to the distal end of the coupling portion 5K. A width L56 of the slit 56K is narrower than the diameter of the guide wire GW which is used in combination. Both sides of the slit 56 in the circumferential direction constitute the suppressor 7K. As shown in FIG. 29, the suppressor 7K is provided at a position covering the proximal end of the sheath slit 23 and the distal end of the proximal end opening 22. A pair of cover bodies 71K are thin and configured to be elastically deformable due to an external force. The slit 56K is an example of a suppression slit.

When the suppressor 7K is in the first state, the sheath slit 23 is covered with the suppressor 7K. Therefore, even when the guide wire GW positioned inside the guide wire lumen 21 is forced to enter the slit 56K and to be exposed to the outside from the suppressor 7K, a large resistance force is generated on the guide wire GW. In particular, the distal end 551K of the guidewire insertion port 55 is located on the proximal side P from the distal end of the proximal end opening 22 of the sheath 2. As a result, the guide wire GW is capable of being prevented from entering the proximal portion of the sheath slit 23.

On the other hand, when the operator wishes to withdraw the guide wire GW from the guide wire lumen 21, applying a larger force to the guide wire GW exposed from the guide wire insertion port 55 to move it radially outward, the guide wire GW enters the slit 56K and can enter the sheath slit 23. As a result, the sheath 2 is smoothly removed while maintaining the state in which the guide wire GW is kept inserted in the body, and shortening of the operation time is achieved.

Sixth Embodiment

Figure 30:
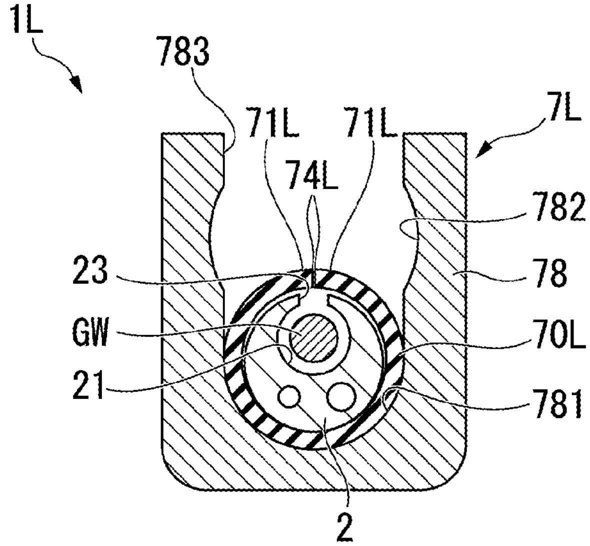
FIG. 30 is a cross-sectional view showing the suppression portion of the treatment tool for an endoscope of a sixth embodiment.
Figure 31:
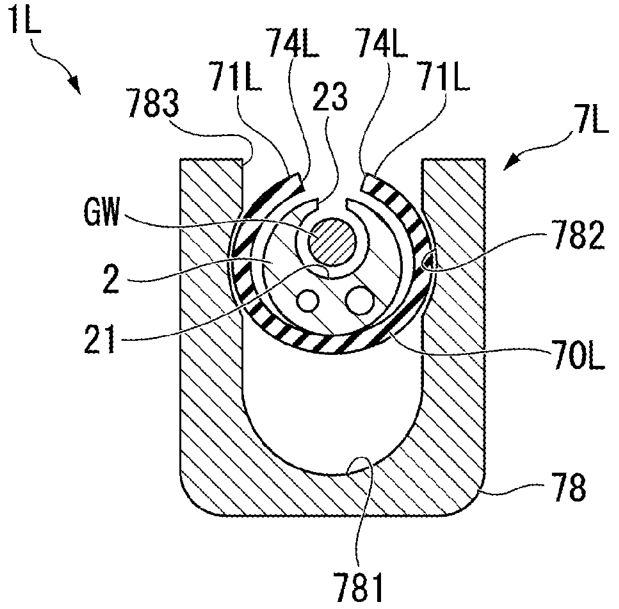
FIG. 31 is a cross-sectional view showing the suppression portion of the treatment tool for an endoscope of the sixth embodiment.

Next, a treatment tool 1L according to a sixth embodiment will be described with reference to FIGS. 30 and 31. FIGS. 30 and 31 are cross-sectional views perpendicular to the longitudinal axis of the sheath 2. FIG. 30 shows a suppressor 7L in the first state. FIG. 31 shows the suppressor 7L in the second state. The suppressor 7L of the treatment tool 1L according to this embodiment includes a cylinder body 70L and a slide member 78. The cylindrical body 70L is formed with an insertion passage that communicates from the distal end to the proximal end in the longitudinal direction. The sheath 2 is inserted through the insertion passage. An open guide wire port is opened in the cylinder body 70L, the same as the cylinder body 70K of the fifth embodiment. A slit 74L extending along the longitudinal axis is formed between the guidewire port and the distal end of the cylinder body 70K. The slit 74L is arranged at a position substantially equal to the sheath slit 23 in the circumferential direction. Cover bodies 71L are arranged on both sides of the slit 74L.

The slide member 78 is slidably provided in a direction orthogonal to the longitudinal axis with respect to the cylindrical body 70L. The slide member 78 has a slide groove having a substantially U-shape in cross section perpendicular to the longitudinal axis. The slide groove has a first groove portion 781 positioned at the bottom of the groove, a third groove portion 783 positioned at approximately an opening end of the slide groove, and a second groove portion 782 provided between the first groove portion 781 and the third groove portion 783. The first groove portion 781 is a groove having approximately the same size as the diameter of the cylindrical body 70L.

As shown in FIG. 30, when the cylindrical body 70L is positioned in the first groove portion 781, the outer surface of the cylindrical body 70L and the first groove portion 781 are in contact with each other, and the pair of cover main bodies 71L are in contact with each other to form the first state. The second groove portion 782 has a larger opening dimension than the first groove portion 781 and the third groove portion 783. The second groove portion 782 is a groove having a size larger than the diameter of the cylinder body 70L.

As shown in FIG. 30, the pair of cover main bodies 71L are positioned to cover the sheath slit 23 when the suppressor 7L is in the first state. As shown in FIG. 31, when the cylindrical body 70L is positioned in the second groove portion 782, the cylindrical body 70L expands radially outward compared with the first state, and the pair of cover main bodies 71L are separated from each other to open the slit 74L. The sheath slit 23 is not covered with the cover main body 71 and the suppressor 7L is in the second state. Since the opening width of the third groove portion 783 is smaller than that of the second groove portion 782, the slide member 78 is less likely to drop out of the cylinder body 70L.

The operator operates the slide member 78 to switch the suppressor 7L between the first state and the second state. When the operator wants to prevent the guide wire GW from entering the sheath slit 23, the operator moves the slide member 78 so that the cylindrical body 70L is arranged in the first groove portion 781. In the first state, since the slit 74L of the cylinder body 70L is closed, the guide wire GW is prevented from entering the sheath slit 23. When removing the guide wire GW from the guide wire lumen 21, the operator moves the slide member 78 in the radial direction of the sheath 2 to arrange the cylindrical body 70L in the second groove portion 782. As a result, the slit 74L of the cylindrical body 70L opens and the sheath slit 23 is opened without being covered. In this state, if the operator moves the exposed portion of the guide wire GW radially outward, the guide wire GW enters the sheath slit 23. In this state, if the proximal portion of the treatment tool 1L is pulled out, the treatment tool 1L is capable of pulling out from the endoscope insertion section 101 while the guide wire GW is indwelled in the body.

According to the treatment tool 1L according to the present embodiment, the suppressor 7L is capable of switching between the first state and the second state by the sliding operation of the slide member 78. Therefore, according to the treatment tool 1L, when the guide wire GW is advanced with respect to the sheath 2, the guide wire GW is prevented from entering the sheath slit 23, and the guide wire GW is smoothly advanced with respect to the sheath 2. On the other hand, when the sheath 2 is removed from the endoscope insertion portion 101, the suppressor 7L is switched to the second state, thereby the sheath 2 is smoothly removed while maintaining the state in which the guide wire GW is kept inserted in the body. As a result, shortening of the operation time is achieved.

Although the slide member 78 that slides in the radial direction of the sheath 2 is exemplarily shown in the above embodiment, the slide member is not limited to the configuration. For example, as in a treatment tool 1M of the modified example shown in FIGS. 32 and 33, a configuration in which a slide member 78M is moved in the longitudinal direction may be employed.

Figure 32:
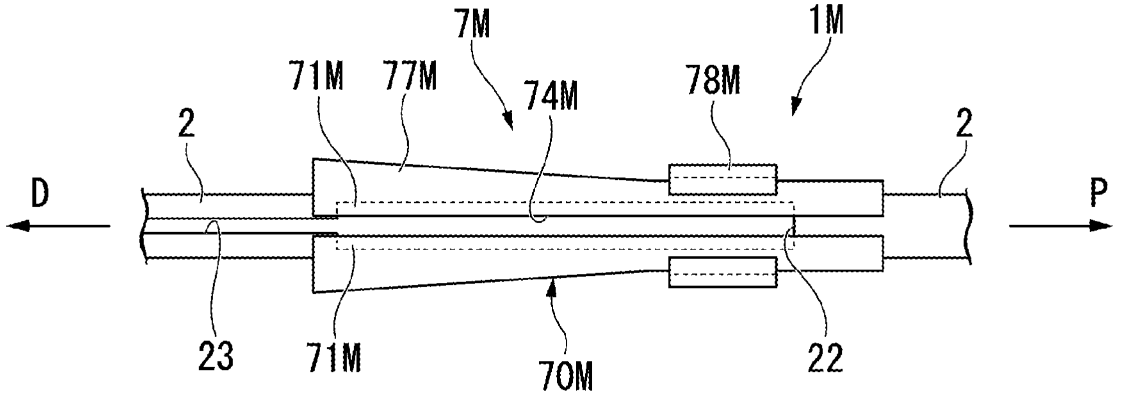
FIG. 32 is a side view showing the suppression portion of the treatment tool for an endoscope of a seventh embodiment.
Figure 33:
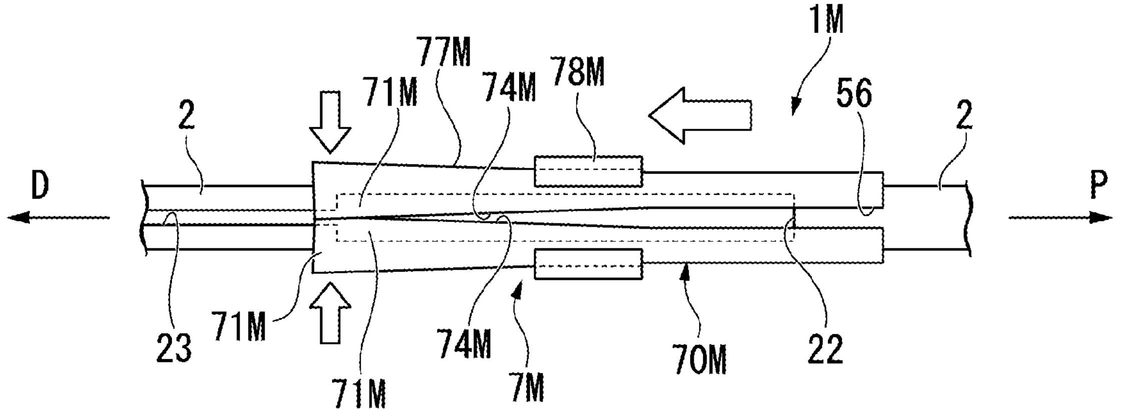
FIG. 33 is a side view showing the suppression portion of the treatment tool for an endoscope of the seventh embodiment.

In the treatment tool 1M shown in FIGS. 32 and 33, a suppressor 7M includes a cylinder body 70M and the slide member 78M. The cylinder body 70M has a tapered portion 77M whose diameter increases toward the distal side D. The distal end of cylinder body 70M has a larger outer diameter than the proximal end. A slit 74M is formed along the longitudinal axis from the distal end to a proximal end of the cylinder body 70M. The slit 74M is arranged at a position corresponding to the sheath slit 23. The slit 74M is an example of a suppression slit. The proximal end opening 22 is opened on the proximal side P of the sheath slit 23 of the sheath 2. The guidewire port 25 has an opening width wider than the sheath slit 23. The cylinder body 70M is longer than the length of the guidewire port 25 of the sheath 2 in the longitudinal direction. The proximal end of the cylinder body 70M is arranged on the proximal side P from the proximal end of the proximal end opening 22 of the sheath 2. The cylinder body 70M is arranged such that the distal end of the cylinder body 70M covers the proximal end of the sheath slit 23 on the distal side D of the proximal end opening 22. A pair of cover main bodies 71M are formed on both circumferential sides of the slit 74M. The pair of cover main bodies 71M cover the boundary between the proximal end of the sheath alit 23 and the proximal end opening 22. The cylinder body 70M is an elastically deformable resin member. The slide member 78M is a C-shaped member which is harder than the cylinder body 70M. The slit 74M is an example of a suppression slit.

The slide member 78M is locked to the outer peripheral portion of the cylinder body 70M. The slide member 78M is provided so as to be slidable from the proximal portion of the cylinder body 70M to the tapered portion 77M. FIG. 32 shows the suppressor 7M in the second state. FIG. 33 shows the suppressor 7M in the first state. When the suppressor 7M is in the second state, the cover body 71M of the cylinder body 70M partially covers the guidewire port 25 of the sheath 2 and forms a gap through which the guidewire GW is passible. When the slide member 78M is moved distally D from the second state, the slide member 78M advances along the tapered portion 77M. Since the cylinder body 70M is elastically deformable, if the slide member 78M moves the tapered portion 77M toward the distal side D, the tapered portion 77M is pushed radially inward and the cover main bodies 71M on both sides of the slit 74M approach each other. When the cover main bodies 71M on both sides approach each other, the slit 74M is elastically deformed so that the opening dimension of the cover main bodies 71M becomes smaller than the opening dimension of the sheath slit 23. As a result, the cover main bodies 71M come into contact with each other, the slit 74M is closed, and the slide member 78M is switched to the first state in which the distal end of the guidewire port 25 and the proximal end of the sheath slit 23 are covered with the cover main body 71M.

According to the treatment tool 1M of the modified example, the same as the treatment tool 1L according to the sixth embodiment, the suppressor 7M is configured to be switchable between the first state and the second state by the sliding operation of the slide member 78M. Therefore, according to the treatment tool 1M, when the guide wire GW is advanced with respect to the sheath 2, the guide wire GW is prevented from entering the sheath slit 23, and the guide wire GW is smoothly advanced with respect to the sheath 2. On the other hand, when the sheath 2 is removed from the endoscope insertion portion 101, the suppressor 7M is switched to the second state, thereby, the sheath 2 is smoothly removed while maintaining the state in which the guide wire GW is kept inserted in the body. As a result, shortening of the operation time is achieved.

Figure 34:
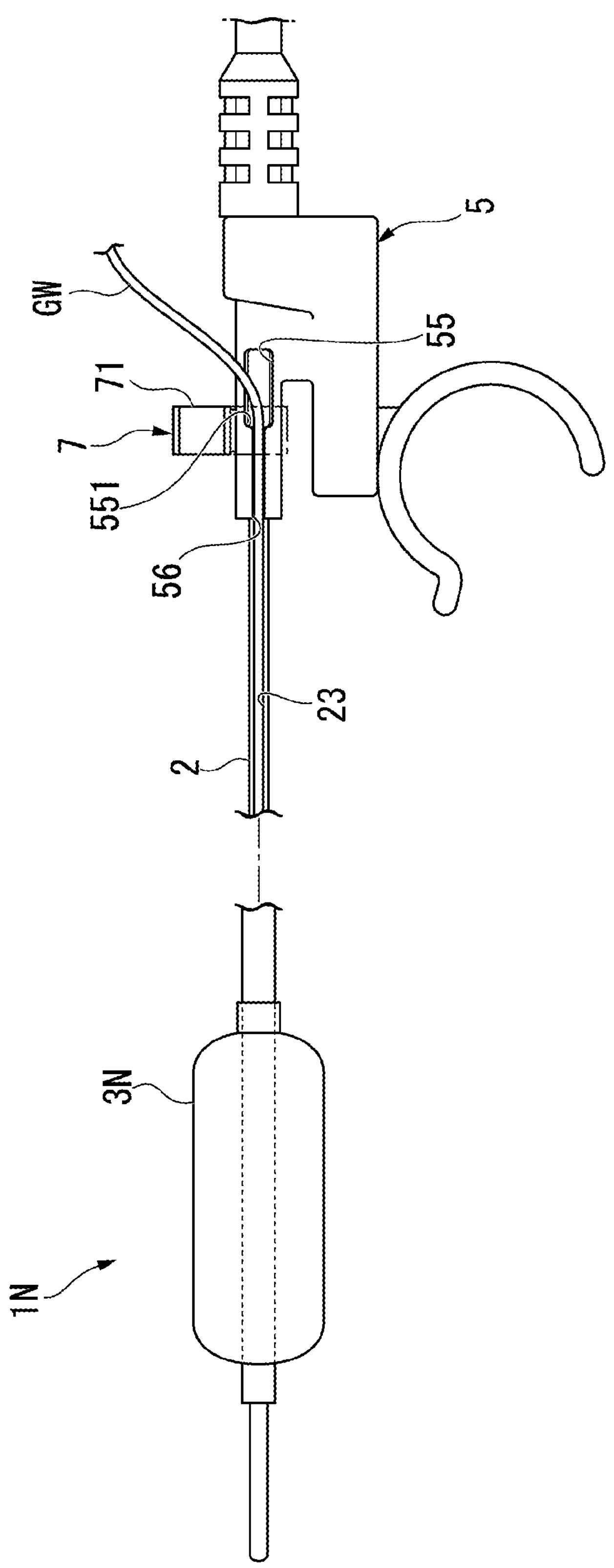
FIG. 34 is a side view showing the treatment tool for an endoscope of the modified example.
Figure 35:
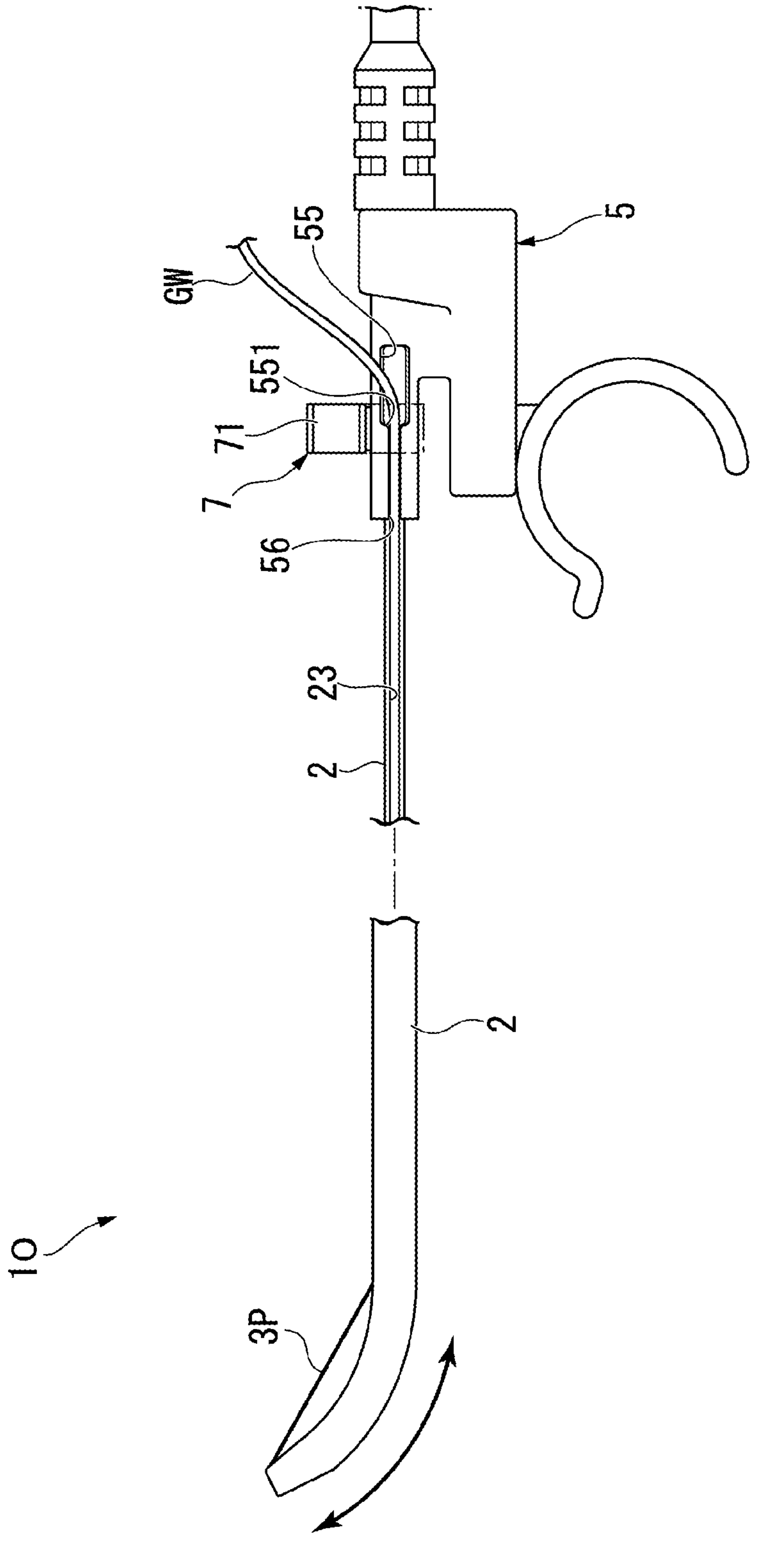
FIG. 35 is a side view showing the treatment tool for an endoscope of the modified example.

Although the treatment tools of the above-described embodiments and modified examples show examples in which the contrast medium is injected into the lumen 29 of the sheath 2, the treatment tools are not limited to these examples. For example, as in a treatment tool 1N shown in FIG. 34, a configuration in which the lumen 29 communicates with a balloon 3N may be employed. FIG. 34 schematically shows enlarged balloon 3N in an enlarged state. For example, as in a treatment tool 1P shown in FIG. 35, a configuration in which a knife wire 3P is inserted through the lumen 29 may be used.

A medical tape wound around the coupling portion 5 may be used as the suppressor. Specifically, a medical tape may be wrapped around a position covering at least one of the sheath slit 23 and the distal end of the proximal end opening 22 in the coupling portion 5 to form the suppressor.

The embodiments of the present invention have been described above. However, the technical scope of the present invention is not limited to the above embodiments, and it is possible to change the combination of elements, make various changes to each element, or delete an element without departing from the gist of the present invention.

What is claimed is:

1. A treatment tool for an endoscope, comprising:

a sheath including a lumen in which a guide wire is insertable, a distal end portion in which a distal end opening is formed on a side surface so as to communicate with the lumen, a proximal end portion in which a proximal end opening communicating with the lumen is formed, and a sheath slit in which a proximal end communicates with the proximal end opening and which is elongated along a longitudinal axis direction toward the distal end portion; and a funnel tube into which the sheath is insertable, the funnel tube including a cylindrical body having a side surface providing a through-hole of the cylindrical body, a funnel portion provided on side surface of the cylindrical body so as to protrude therefrom and having a proximal opening communicating with the through-hole of the cylindrical body, and a first funnel slit provided in the cylindrical body and a second funnel slit provided in the funnel portion and extending along the longitudinal axis, wherein the funnel tube is capable of changing between a first state and a second state by rotating about the longitudinal axis with respect to the sheath, in the first state, the guide wire is restricted to enter the sheath slit, and in the second state, the guide wire is capable of being inserted into the sheath slit, and the proximal end opening of the sheath and the through-hole of the cylindrical body communicate with each other in both the first state and the second state.

2. The treatment tool for an endoscope according to claim 1, wherein in the first state, positions of the first funnel slit and the second funnel slit are different from the sheath slit in a circumferential direction, wherein in the second state, the positions of the first funnel slit and the second funnel slit are substantially alike with the sheath slit in the circumferential direction.

* * * * *